(12) United States Patent
Hashimoto et al.

(10) Patent No.: US 8,642,191 B2
(45) Date of Patent: Feb. 4, 2014

(54) FUSED POLYCYCLIC COMPOUND AND ORGANIC LIGHT-EMITTING ELEMENT

(75) Inventors: Masashi Hashimoto, Tokyo (JP); Yuko Chishina, Tokyo (JP); Kengo Kishino, Tokyo (JP); Satoshi Igawa, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 98 days.

(21) Appl. No.: 13/131,460

(22) PCT Filed: Nov. 25, 2009

(86) PCT No.: PCT/JP2009/070202
§ 371 (c)(1),
(2), (4) Date: May 26, 2011

(87) PCT Pub. No.: WO2010/061952
PCT Pub. Date: Jun. 3, 2010

(65) Prior Publication Data
US 2011/0260151 A1    Oct. 27, 2011

(30) Foreign Application Priority Data

Nov. 28, 2008  (JP) .................................. 2008-304601
Oct. 26, 2009  (JP) .................................. 2009-245813

(51) Int. Cl.
*H01L 51/54* (2006.01)

(52) U.S. Cl.
USPC ............ 428/690; 428/917; 313/504; 313/506

(58) Field of Classification Search
None
See application file for complete search history.

(56) References Cited

U.S. PATENT DOCUMENTS 6,187,457 B1 *  2/2001  Arai et al. ..................... 428/690
7,189,466 B2 *  3/2007  Moriyama et al. ............ 428/690

(Continued)

FOREIGN PATENT DOCUMENTS

JP      10-294177 A    11/1998
JP      10-330295 A    12/1998

(Continued)

OTHER PUBLICATIONS

Translation for JP 2009-009966 A (published Jan. 2009).*

(Continued)

*Primary Examiner* — Dawn L. Garrett
(74) *Attorney, Agent, or Firm* — Canon USA, Inc. IP Division

(57) ABSTRACT

A fused polycyclic compound is represented by general formula [1]:

[Chem. 1]

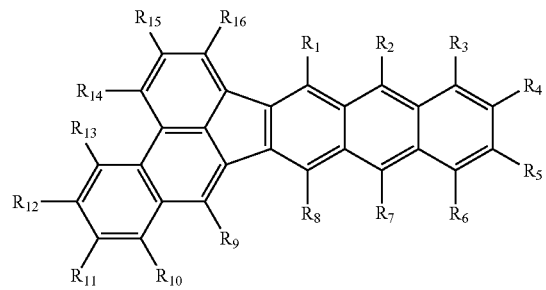

wherein at least one of $R_1$ to $R_{16}$ is selected from a halogen atom, an alkyl group having 1 to 20 carbon atoms, a substituted amino group, an aryl group which may have a substituent, and a heterocyclic group which may have a substituent. An organic light-emitting element includes the fused polycyclic compound.

22 Claims, 2 Drawing Sheets

(56) References Cited

U.S. PATENT DOCUMENTS

2004/0076853 A1* 4/2004 Jarikov .................. 428/690
2005/0030264 A1* 2/2005 Tsuge et al. ................ 345/76

FOREIGN PATENT DOCUMENTS

| JP | 2002-8867 A | 1/2002 |
| JP | 2005-53806 A | 3/2005 |
| JP | 2009-009966 A | 1/2009 |
| WO | 2007/099983 A | 9/2007 |

OTHER PUBLICATIONS

Journal of Molecular Structure, 362, 29-49 (1996).

* cited by examiner

FUSED POLYCYCLIC COMPOUND AND ORGANIC LIGHT-EMITTING ELEMENT

TECHNICAL FIELD

The present invention relates to a novel fused polycyclic compound and an organic light-emitting element including the same.

BACKGROUND ART

Recently, organic light-emitting elements have become markedly advanced. Features of organic light-emitting elements include the high luminance achieved by a low applied voltage, a variety of emission wavelengths, a high-speed responsiveness, and the possibility of realization of a thin, lightweight light-emitting device. Accordingly, the possibility of a wide variety of applications has been suggested for organic light-emitting elements.

However, under the present situation, an optical output with a higher luminance and higher conversion efficiency are necessary. Furthermore, there are still a lot of problems in terms of durability, for example, a change with time due to long-term use and degradation due to an atmospheric gas containing oxygen, moisture, or the like. Furthermore, considering the application to a full-color display or the like, light emission of blue, green, and red having good color purity is necessary, but technologies related to these issues have not yet satisfactorily been developed.

A large number of aromatic compounds and fused-ring aromatic compounds have been studied as fluorescent organic compounds used as an electron-transporting layer, a light-emitting layer, or the like. However, compounds having satisfactorily high light-emission luminance and durability have not yet been developed.

Fused-ring aromatic compounds have been investigated in various fields, and Non Patent Citation 1 has reported the carcinogenic potential and reactivity of such compounds.

Furthermore, Patent Citations 1 to 4 disclose examples in which an aromatic compound or a fused-ring aromatic compound is used as a material constituting an organic light-emitting element. Patent Citations 1 to 4 disclose an application of fused polycyclic materials to organic light-emitting elements.
Non Patent Citation 1
Journal of Molecular Structure, 362, 29-49 (1996)
Patent Citation 1
Japanese Patent Laid-Open No. 2002-8867
Patent Citation 2
Japanese Patent Laid-Open No. 10-330295
Patent Citation 3
Japanese Patent Laid-Open No. 10-294177
Patent Citation 4
Japanese Patent Laid-Open No. 2005-53806

DISCLOSURE OF INVENTION

To apply an organic light-emitting element to a display apparatus such as a display, it is necessary that the organic light-emitting element have luminous characteristics with high efficiency and sufficient durability.

The present invention provides a novel fused polycyclic compound having luminous characteristics with high efficiency and high durability. The present invention further provides an organic light-emitting element including such a fused polycyclic compound and having luminous characteristics with high efficiency and high durability. Furthermore, the present invention provides a light-emitting element which can be easily produced with relatively low cost.

Specifically, the present invention provides a fused polycyclic compound represented by general formula [1].

[Chem. 1]

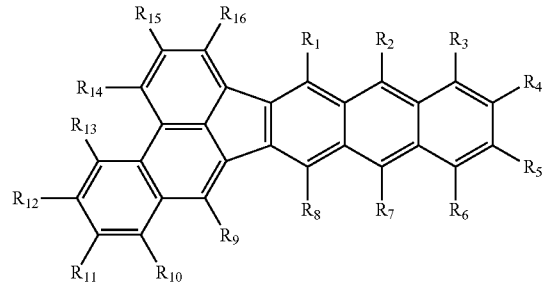

[1]

In general formula [1], $R_1$ to $R_{16}$ are each independently selected from a hydrogen atom, a halogen atom, an alkyl group having 1 to 20 carbon atoms, a substituted amino group, an aryl group which may have a substituent, and a heterocyclic group which may have a substituent. However, at least one of $R_1$ to $R_{16}$ is selected from a halogen atom, an alkyl group having 1 to 20 carbon atoms, a substituted amino group, an aryl group which may have a substituent, and a heterocyclic group which may have a substituent.

The present invention provides an organic light-emitting element including the above fused polycyclic compound.

The present invention can provide a fused polycyclic compound with high durability. Accordingly, an organic light-emitting element having high durability can be provided. Furthermore, the light-emitting element of the present invention can be provided as a display apparatus.

DESCRIPTION OF EMBODIMENTS

Figure 1:
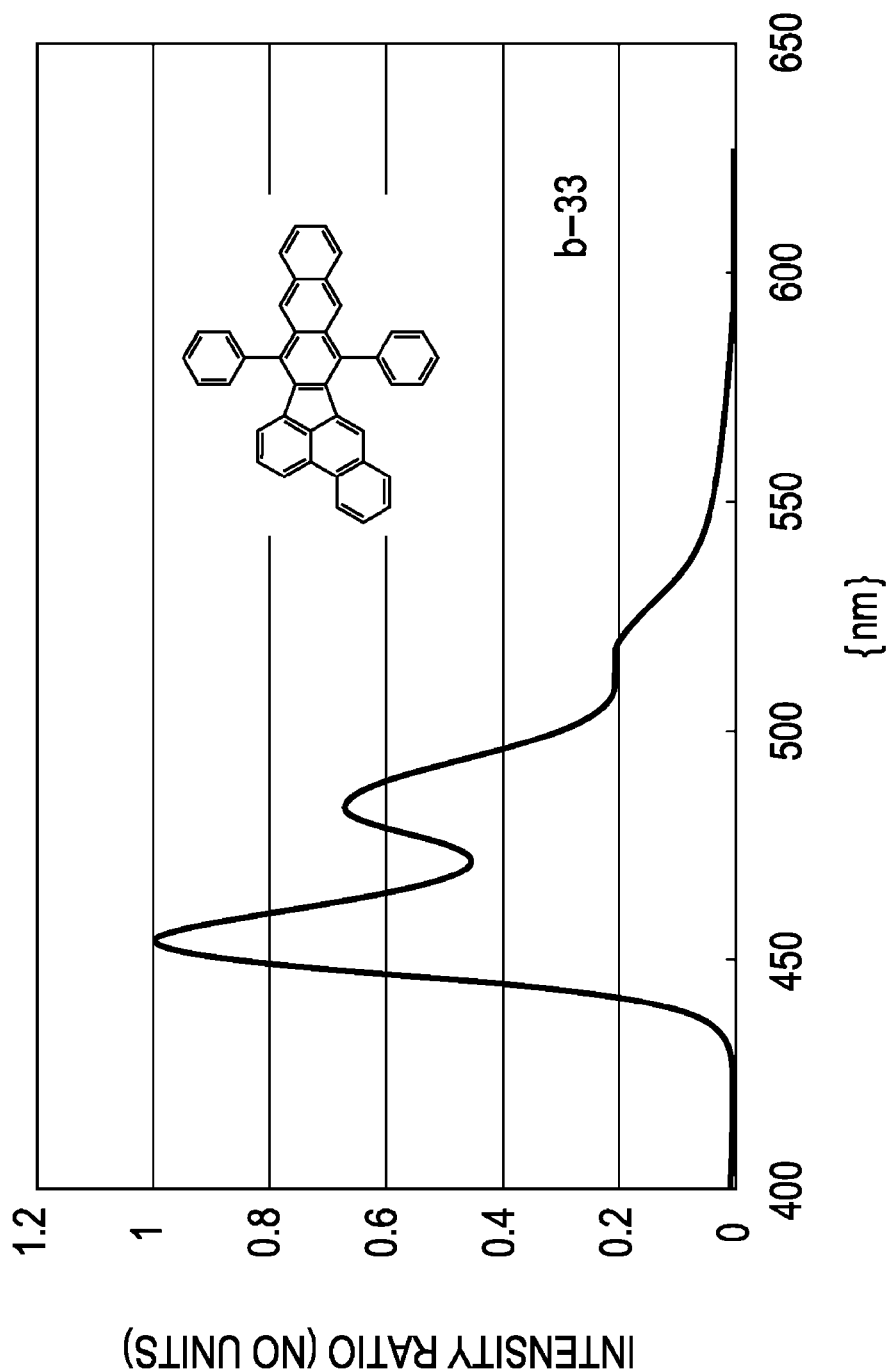
FIG. 1 shows an emission spectrum of Exemplified Compound b-33.

A fused polycyclic compound according to the present invention is represented by general formula [1] below.

[Chem. 2]

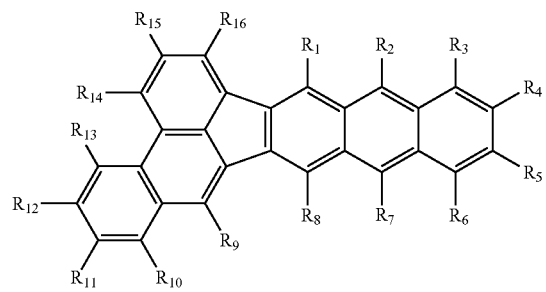

[1]

In general formula [1], $R_1$ to $R_{16}$ are each independently selected from a hydrogen atom, a halogen atom, an alkyl group having 1 to 20 carbon atoms, a substituted amino group, an aryl group which may have a substituent, and a heterocyclic group which may have a substituent. However, at least one of $R_1$ to $R_{16}$ is selected from a halogen atom, an alkyl group having 1 to 20 carbon atoms, a substituted amino group, an aryl group which may have a substituent, and a heterocyclic group which may have a substituent.

Herein, examples of the halogen atom include a fluorine atom, a chlorine atom, and a bromine atom. When an organic light-emitting element is prepared by a vacuum evaporation method, among these halogen atoms, a fluorine atom is particularly preferable in view of sublimability.

Examples of the alkyl group having 1 to 20 carbon atoms include a methyl group, an ethyl group, a n-propyl group, an isopropyl group, a n-butyl group, a tert-butyl group, an octyl group, and a cyclohexyl group. When the number of carbons is two or more, one methylene group or two or more methylene groups that are not adjacent to each other may be substituted with —O— to form a methoxy group, an ethoxy group, or the like. Furthermore, hydrogen atoms in the alkyl group may be substituted with fluorine atoms to form a trifluoromethyl group or the like.

From the standpoint of the electrical conductivity and sublimability, among these alkyl groups, a methyl group, a tert-butyl group, a cyclohexyl group, and a trifluoromethyl group are preferable. A methyl group, a tert-butyl group, and a trifluoromethyl group are more preferable. A tert-butyl group is further preferable.

From the standpoint of the electrical conductivity and the glass transition temperature, the substituted amino group is, for example, a dimethylamino group, a diphenylamino group, and a ditolylamino group. A particularly preferable example is a diphenylamino group.

Examples of the aryl group which may have a substituent include a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, and a perylenyl group.

From the standpoint of sublimability, a phenyl group, a biphenyl group, a fluorenyl group, and a naphthyl group are preferable. A phenyl group and a biphenyl group are more preferable.

Examples of the heterocyclic group which may have a substituent include a thienyl group, a pyrrolyl group, a pyridyl group, a pyrazyl group, a pyrimidyl group, a pyridazinyl group, a quinolinyl group, an isoquinolinyl group, a phenanthrydinyl group, an acridinyl, a naphthylidinyl group, a quinoxalinyl group, a quinazolinyl group, a cinnolinyl group, a phthalazinyl group, a phenanthrolyl, a phenazinyl group, a dibenzofuranyl group, a dibenzothiophenyl group, a carbazolyl group, a benzofuranyl group, a benzothiophenyl group, indolyl group, a cycloazyl group, a benzimidazolyl group, a benzothiazolyl group, and a benzothiadiazolyl group. From the standpoint of sublimability, a pyridyl group is preferable.

Examples of the substituent which may be included in the aryl group and the heterocyclic group include, but are not particularly limited to, halogen atoms, alkyl groups having 1 to 20 carbon atoms, and substituted amino groups. When the number of carbons of the alkyl group is two or more, one methylene group or two or more methylene groups that are not adjacent to each other may be substituted with —O—. Furthermore, hydrogen atoms of the alkyl group may be substituted with fluorine atoms. Specific examples of the halogen atoms, the alkyl groups, and the substituted amino groups are the same as the above-mentioned specific examples of the halogen atoms, the alkyl groups, and the substituted amino groups which are substituents introduced to $R_1$ to $R_{16}$.

Among these substituents, from the standpoint of the glass transition temperature and sublimability, a fluorine atom, a trifluoromethyl group, a methyl group, an ethyl group, a tert-butyl group, a methoxy group, a dimethylamino group, a di-tert-butylamino group, and a phenyl group are preferable. A fluorine atom, a trifluoromethyl group, a methyl group, a tert-butyl group, and a phenyl group are more preferable. A tert-butyl group and a phenyl group are particularly preferable.

The fused polycyclic compound according to the present invention particularly preferably has a structure constituted by only carbon atoms and hydrogen atoms. This is because such a molecule constituted by only carbon atoms and hydrogen atoms may suppress the incorporation of ionic impurities or the like, which are believed to be a possible cause of energization degradation of an organic light-emitting element, as compared with a compound containing a heteroatom having a lone pair of electrons. Suppressing the incorporation of ionic impurities can improve the lifetime of the organic light-emitting element.

In the fused polycyclic compound according to the present invention, at least one of $R_1$ to $R_{16}$ is preferably selected from a halogen atom, an alkyl group having 1 to 20 carbon atoms, a substituted amino group, an aryl group which may have a substituent, and a heterocyclic group which may have a substituent.

As a substituent introduced, an aryl group which may have a substituent or a heterocyclic group which may have a substituent is preferable, and an aryl group is more preferable.

A substituent is preferably introduced to at least one of $R_1$, $R_2$, $R_7$, and $R_8$ among $R_1$ to $R_{16}$. More preferably, substituents are introduced to either a pair of $R_2$ and $R_7$ or a pair of $R_1$ and $R_8$. Further preferably, the same substituent is introduced to either the pair of $R_2$ and $R_7$ or the pair of $R_1$ and $R_8$. Further preferably, the same substituent is introduced to the pair of $R_1$ and $R_8$.

The skeleton structure represented by general formula [1] has a substantially complete planar structure.

Each of the substitution positions of $R_1$, $R_2$, $R_7$, and $R_8$ is a position that is strongly subjected to steric repulsion from the positions of both adjacent substituents. As a result, when a substituent is introduced to any of these positions and the substituent is a substituent having a planar structure, e.g., an aryl group or a heterocyclic group, the plane of the substituent is disposed substantially orthogonal to the plane of the skeleton structure represented by general formula [1]. Consequently, a stacking property of the molecules can be suppressed.

Also in the case where a planar substituent is bonded to $R_{13}$ or $R_{14}$, it is believed that the substitution position is strongly subjected to steric repulsion in theory. However, from the standpoint of the suppression of molecular stacking, the substituent is preferably introduced to at least one position of $R_1$, $R_2$, $R_7$, and $R_8$, which are located at the center of the molecular skeleton.

Note that it is believed that when a planar substituent is bonded to $R_9$, the substitution position is also strongly subjected to steric repulsion in theory. However, it is very difficult to provide a substituent to this position in view of synthesis.

In addition, it is desirable that the substituents are introduced to the positions of the pair of $R_2$ and $R_7$ or the pair of $R_1$ and $R_8$ because a compound having such a structure can be easily synthesized.

The degree of an increase in steric repulsion due to the plane of a substituent relative to the skeleton structure represented by general formula [1] varies depending on the substitution position.

According to a study conducted by the inventors of the present invention, the degree of steric repulsion is approximately represented by the following relationship depending on the position of a substituent:

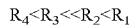

Accordingly, a planar substituent is bonded to preferably $R_2$ or $R_1$, and more preferably $R_1$.

In view of the simplicity of synthesis, when a substituent is provided at $R_2$, a substituent is also preferably provided at $R_7$. Similarly, when a substituent is provided at $R_1$, a substituent is also preferably provided at $R_8$.

Furthermore, when a substituent is provided to the skeleton structure represented by general formula [1], chemical and physical properties due to the skeleton structure represented by general formula [1] should not be significantly changed.

In order to decrease only the stacking property of the whole molecule without significantly changing such properties, a planar substituent is preferably provided as a substituent at a specific position. In addition, the number of substituents provided to the skeleton structure represented by general formula [1] is preferably small. Among exemplified compounds having structural formulae shown below, compounds, the name of which includes symbol b, that is, compounds two planar substituents are provided in the skeleton structure represented by general formula [1] are more preferable.

It is assumed that the exemplified compound represented by b-17 has two planes that are bonded directly to the skeleton structure represented by general formula [1]. That is, in b-17, one plane of a naphthalene ring is directly bonded to the skeleton structure represented by general formula [1] and two naphthalene rings are bonded to the skeleton structure in b-17. Accordingly, it is assumed that two planes are respectively bonded to the skeleton structure represented by general formula [1]. Similarly, this also applies to b-30 etc. On the basis of this idea, the exemplified compounds having the structural formulae shown below are classified into groups with the same symbol.

Compounds, the name of which includes symbol a, are compounds in which one plane is bonded to the skeleton structure represented by general formula [1].

As the symbols continue to c, d, e, f, g, h, i, and j, the number of planes bonded to the skeleton structure represented by general formula [1] increases one by one. Compounds having a name including symbol k are other possible exemplified compounds containing elements other than carbon and hydrogen.

By introducing a substituent so as to be orthogonal to the skeleton structure represented by general formula [1], the stacking property of the molecule is decreased. Consequently, the following three advantages can be expected.

(1) An improvement in the stability of an organic thin film due to a decrease in the crystallinity can be expected. Accordingly, it is expected that a light-emitting element including, as a host material or a guest material of a light-emitting layer, a fused-ring compound of the present invention can suppress emission degradation due to energization. This is because crystallization of organic compounds is one possible cause of emission degradation due to energization in an electroluminescence element.

(2) Suppression of concentration quenching (a phenomenon in which when the concentration of a guest material in a light-emitting element increases, the luminous efficiency decreases) can be expected. This is because it is believed that quenching due to stacking of the same type of molecules and the formation of an excimer can be suppressed by suppressing a stacking property of molecules. Accordingly, when such a compound is used as a luminescent material, a decrease in the luminous efficiency and a change in the luminescent color can be suppressed.

(3) An improvement in the sublimability can be expected. This is because it is believed that the sublimation temperature is decreased by decreasing intermolecular interaction. Accordingly, it is believed that sublimation purification can be used as a method of purifying the compound, and thermal decomposition of the material can be suppressed when an organic light-emitting element is produced by a vacuum evaporation method.

In order to achieve the above advantages (1) to (3) more effectively, substituents are more preferably introduced to two positions or more, as described above.

It is believed that if the molecular weight of the compound is too high, the sublimation temperature increases, thereby increasing the probability of thermal decomposition of the compound during vacuum evaporation. From the standpoint of the advantages (1) to (3) above and sublimability, the number of substituents is preferably in the range of 2 to 6, more preferably in the range of 2 to 4, and particularly preferably 2, as described above.

A fused polycyclic compound according to the present invention can be synthesized by, for example, synthetic routes shown below.

However, the present invention is not limited thereto.

[Chem. 3]
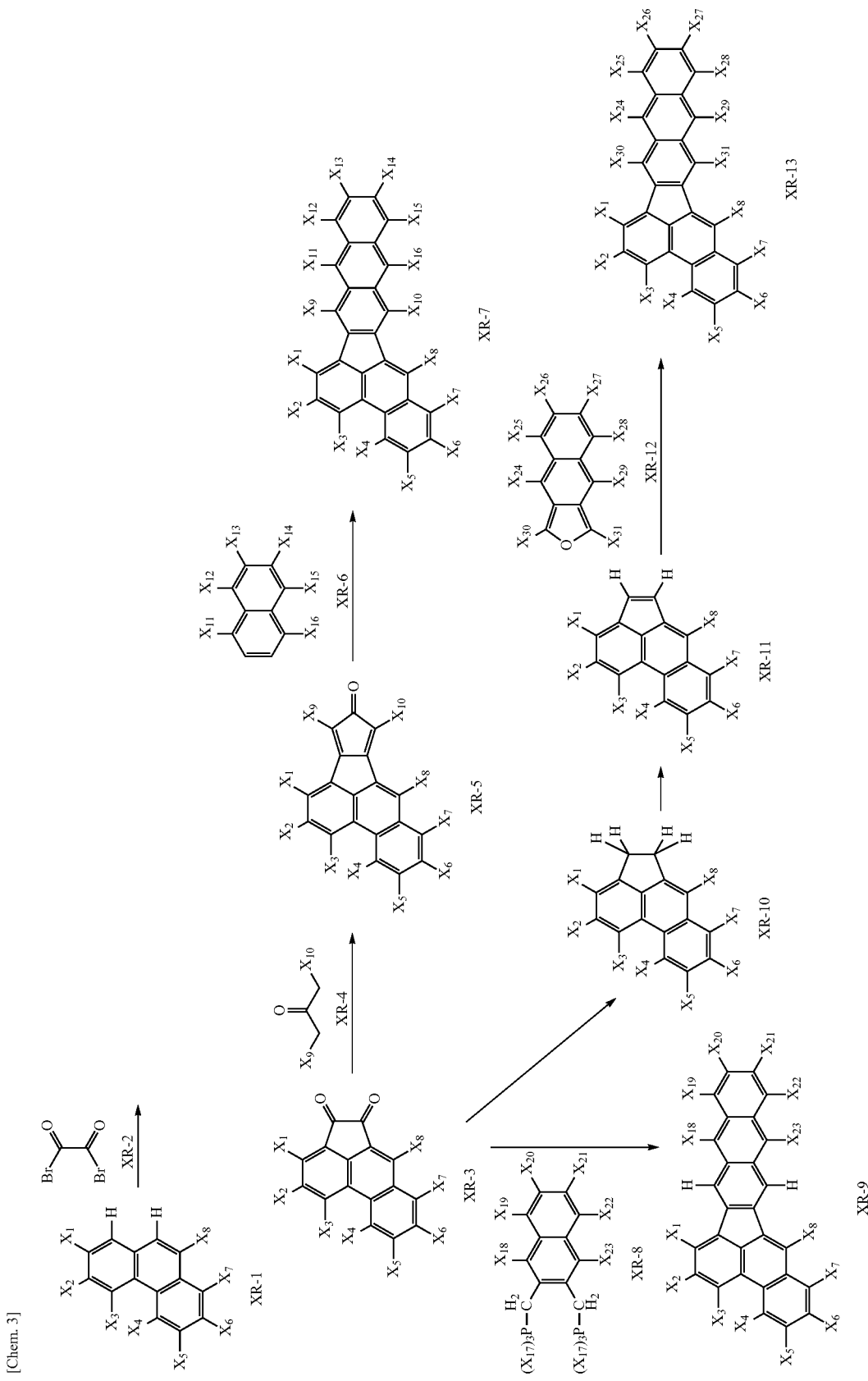

In the above synthetic routes, from the standpoint of the stability of a synthetic intermediate product XR-5 and XR-12, each of $X_9$, $X_{10}$, $X_{30}$, and $X_{31}$ is preferably an aryl group.

That is, each of $R_1$ and $R_8$ in general formula [1] is preferably an aryl group.

When $X_9$ and $X_{10}$ in XR-4 are the same, the number of stages of synthesizing the compound can be decreased and the processes of synthesis and purification can be simplified, as compared with the case where $X_9$ and $X_{10}$ in XR-4 are different from each other.

Also, when $X_{30}$ and $X_{31}$ in XR-12 are the same, the number of stages of synthesizing the compound can be decreased and the processes of synthesis and purification can be simplified, as compared with the case where $X_{30}$ and $X_{31}$ in XR-12 are different from each other.

That is, it is believed that when $R_1$ and $R_8$ in general formula [1] are the same aryl group, the compound can be produced at a lower cost.

Preferably, a fused polycyclic compound according to the present invention is sufficiently purified to remove impurities.

An example of the cause of emission degradation due to energization is mixing of impurities. When a polymer compound is used as a material constituting an element, it is difficult to remove impurities contained in the polymer, and thus the impurities are readily mixed in the element, resulting in a decrease in the lifetime of the element. In contrast, since a fused polycyclic compound according to the present invention is a single compound, impurities therein can be easily removed by appropriately employing a purification method such as recrystallization, column chromatography, or sublimation purification. Accordingly, the use of a fused polycyclic compound according to the present invention as a material constituting an organic light-emitting element improves the durability of the organic light-emitting element.

Specific examples of the fused polycyclic compound according to the present invention are shown below. However, the compounds shown below are only illustrative, and the fused polycyclic compound according to the present invention is not limited thereto.

[Chem. 4]

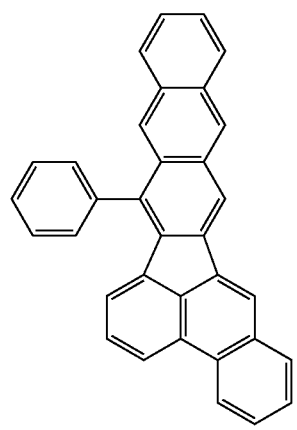

a-1

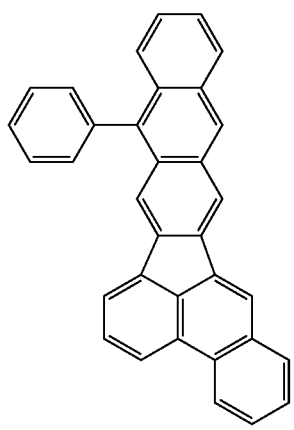

a-2

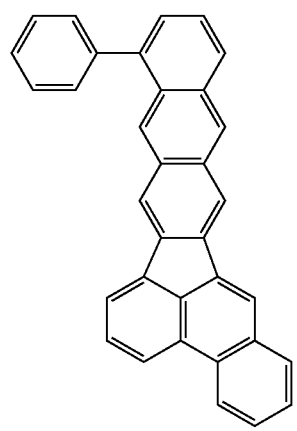

a-3

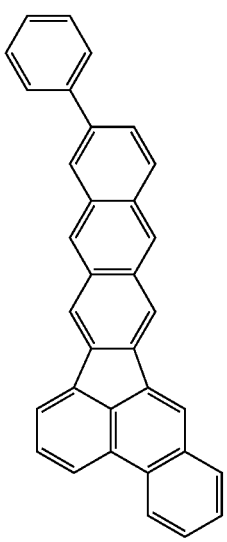

a-4

-continued
a-5
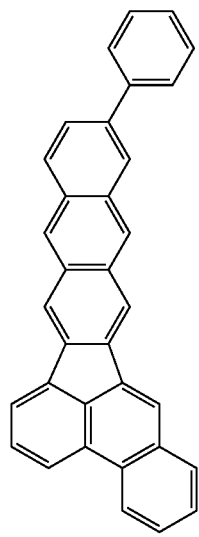
a-6
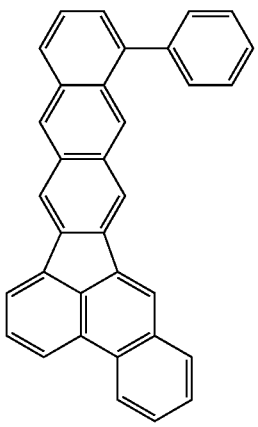
a-7
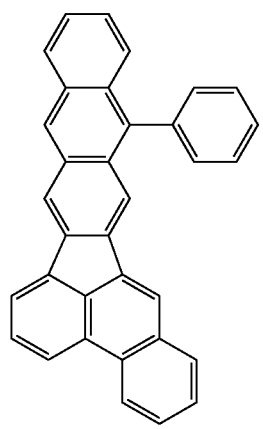
a-8
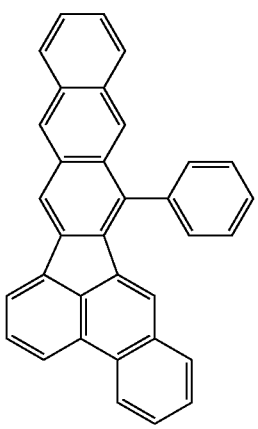
a-9
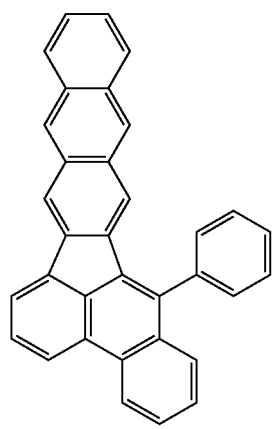
a-10
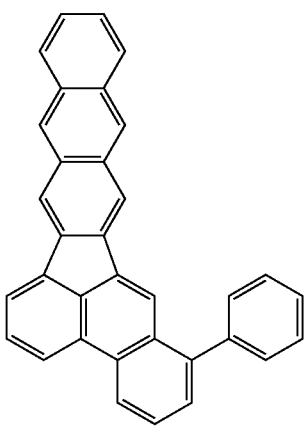

a-11
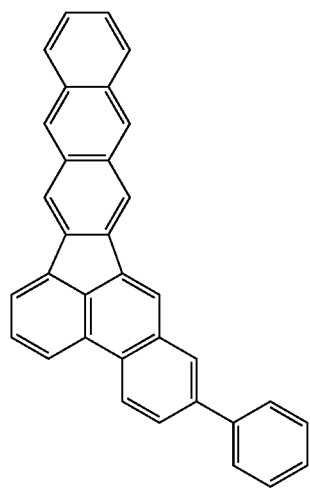
a-12
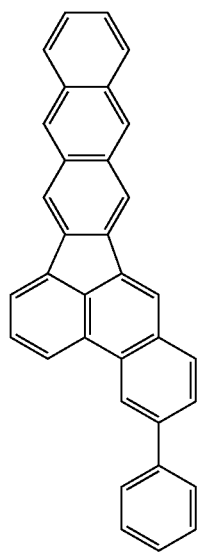
a-13
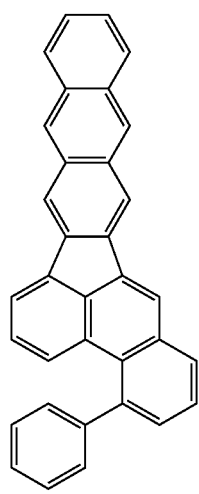
a-14
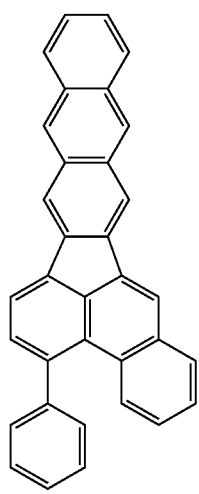
a-15
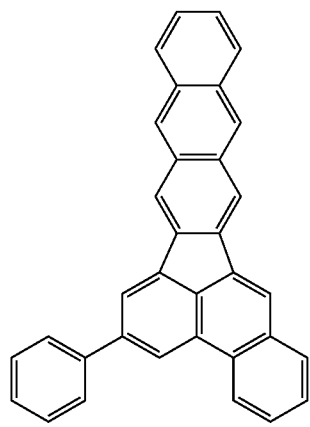

[Chem. 5]
a-16
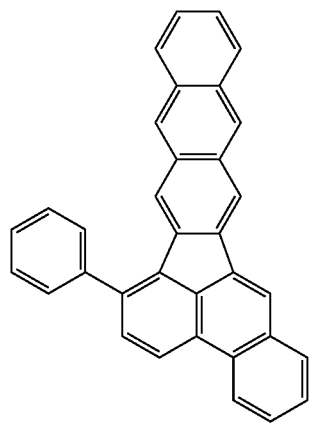
a-17
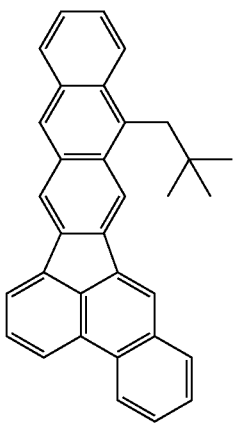
a-18
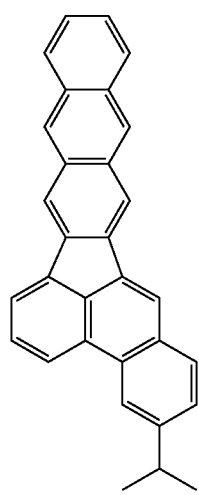
a-19
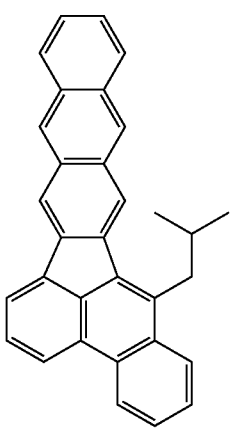
a-20
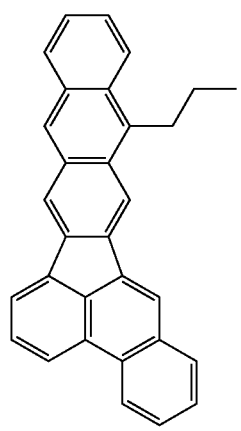
a-21
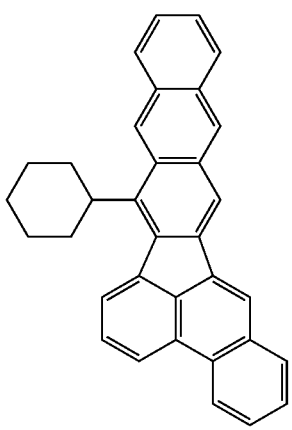

-continued
a-22
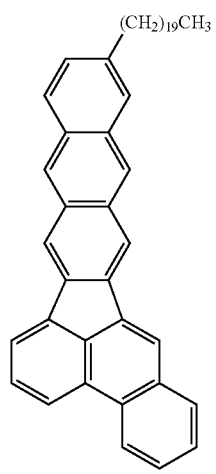
a-23
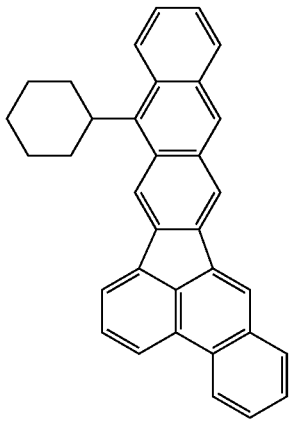
[Chem. 6]
b-1
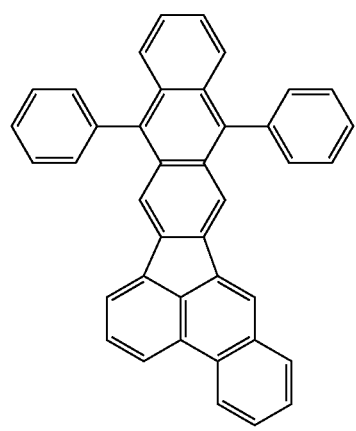
b-2
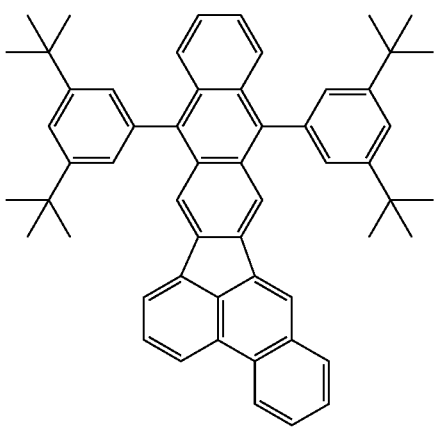
b-3
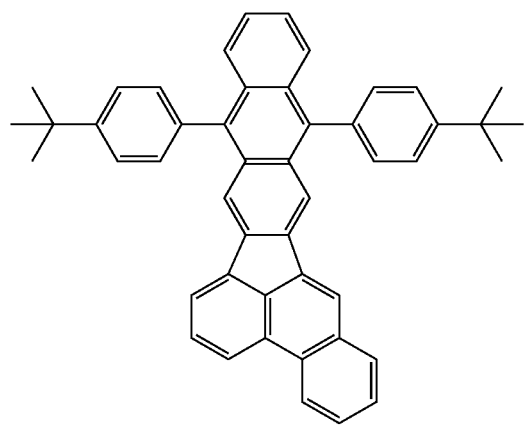
b-4
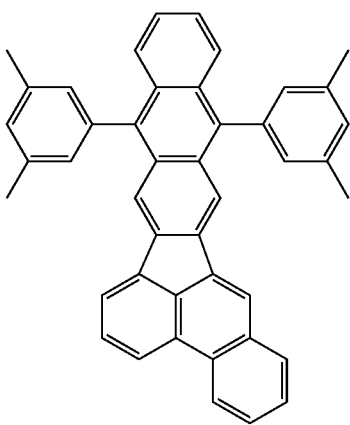

-continued
b-5
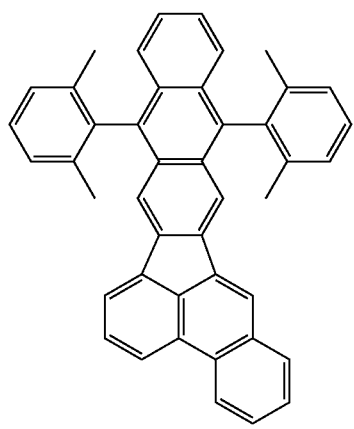
b-6
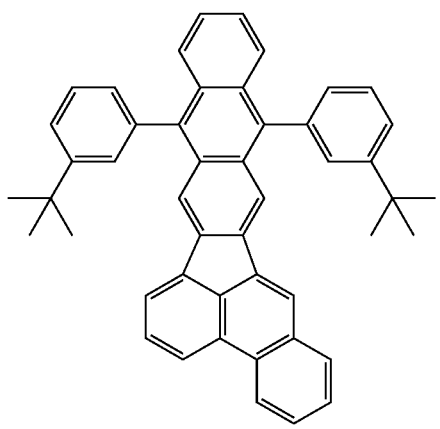
b-7
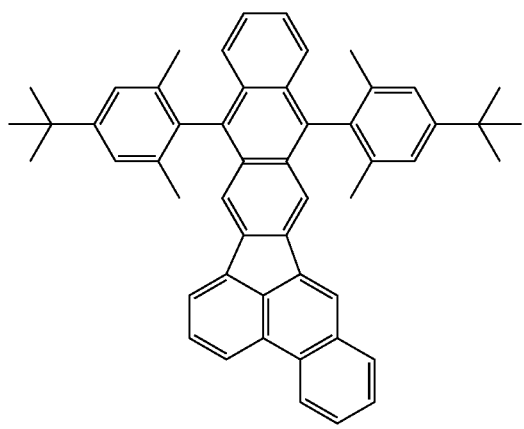
b-8
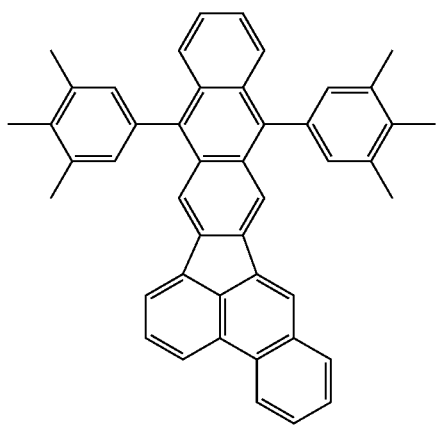
b-9
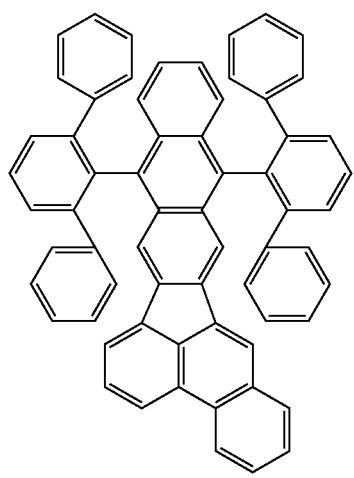
b-10
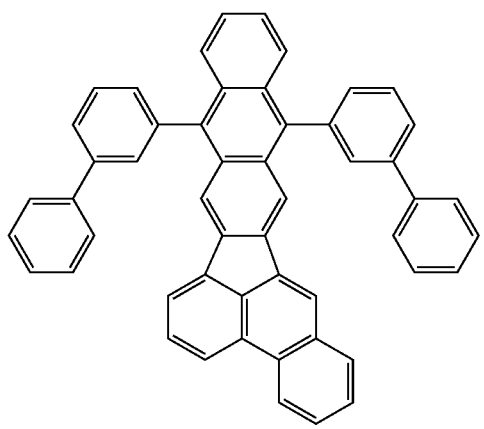

-continued
b-11
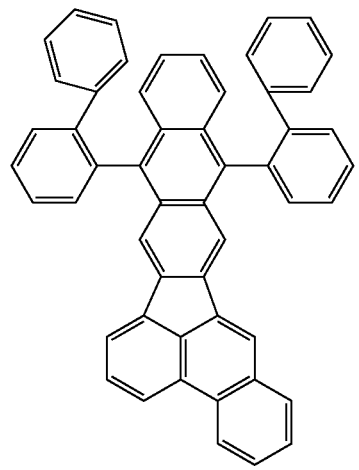
b-12
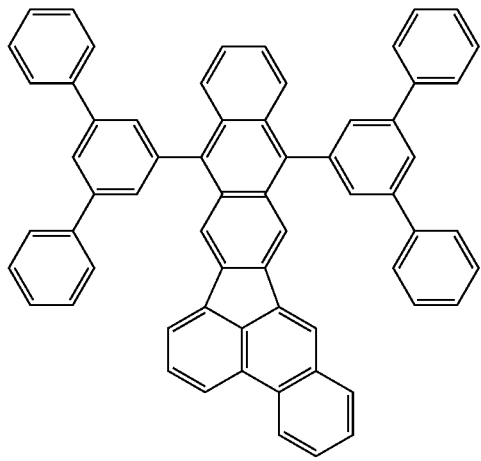
b-13
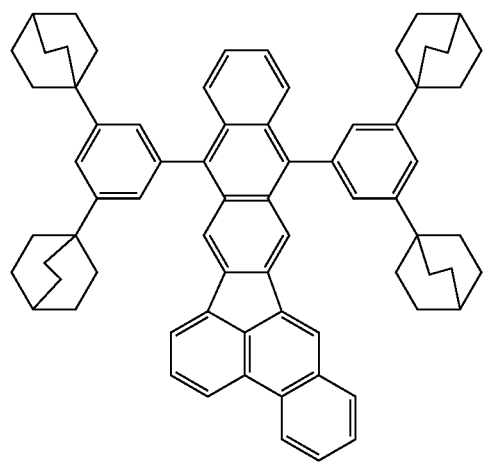
b-14
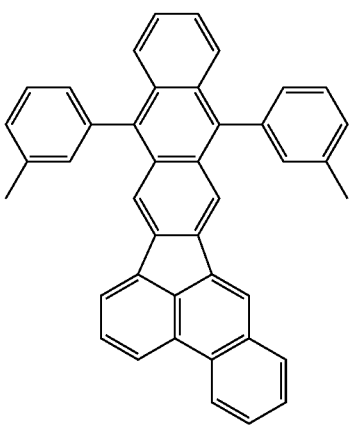
b-15
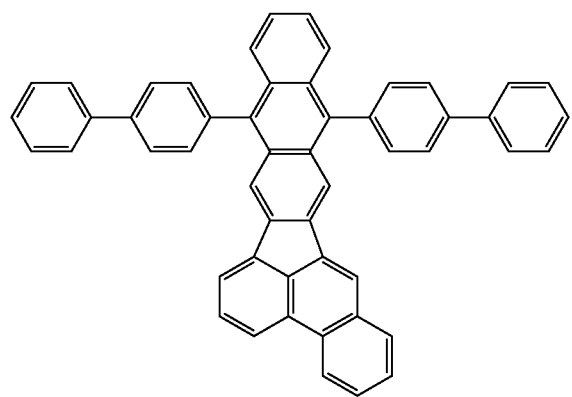
b-16
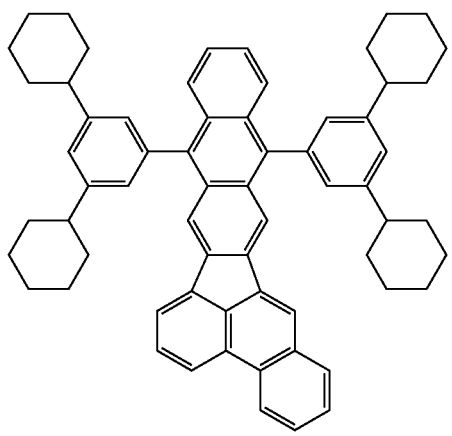

[Chem. 7]
b-17
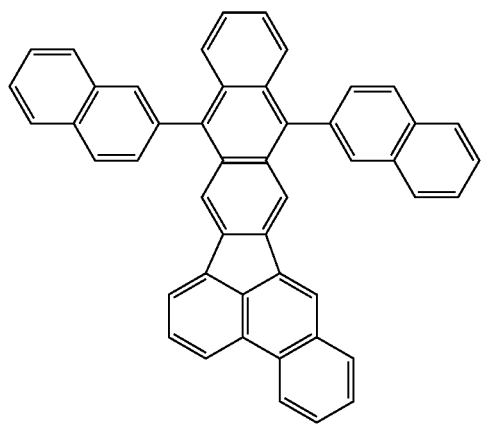
b-18
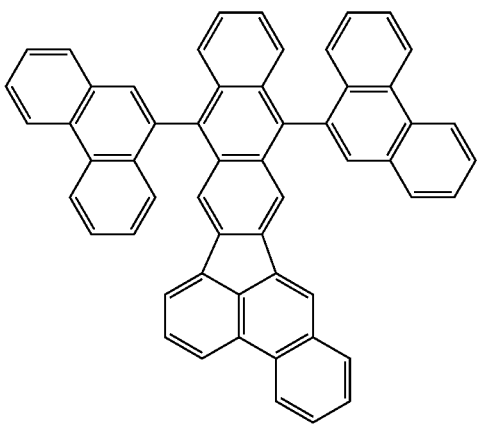
b-19
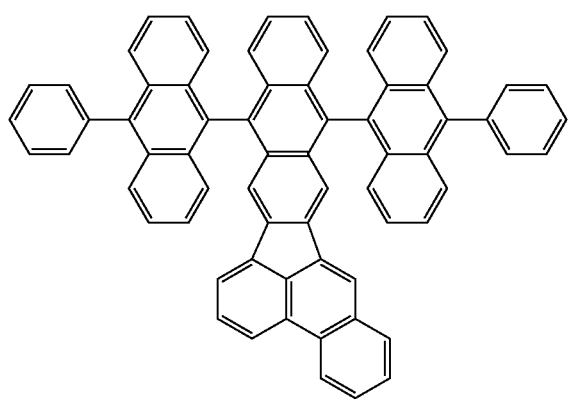
b-20
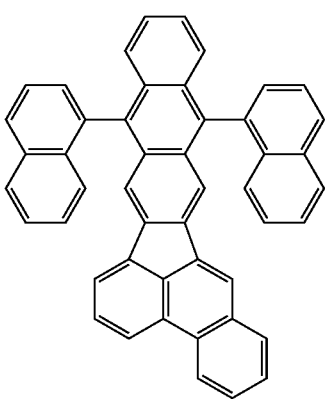
b-21
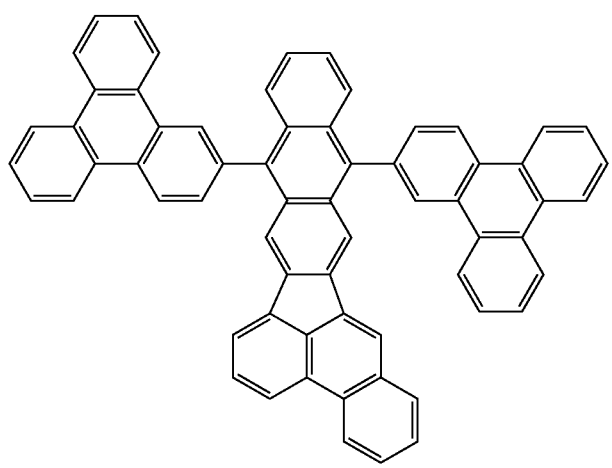

-continued
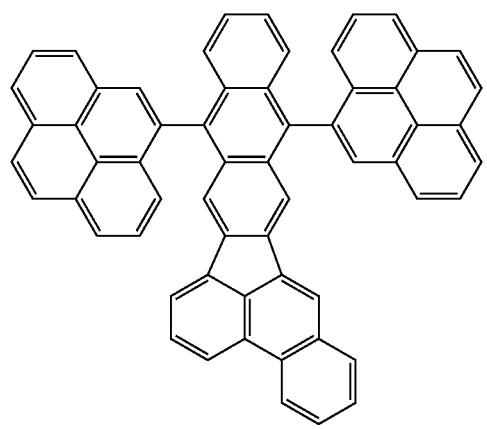
b-22
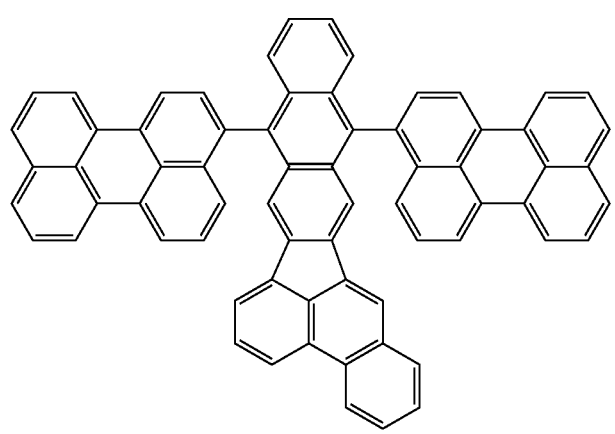
b-23
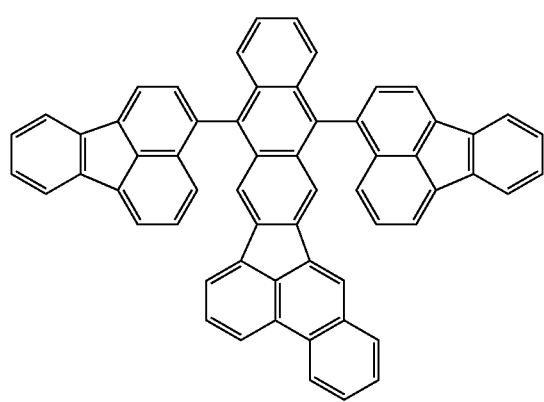
b-24
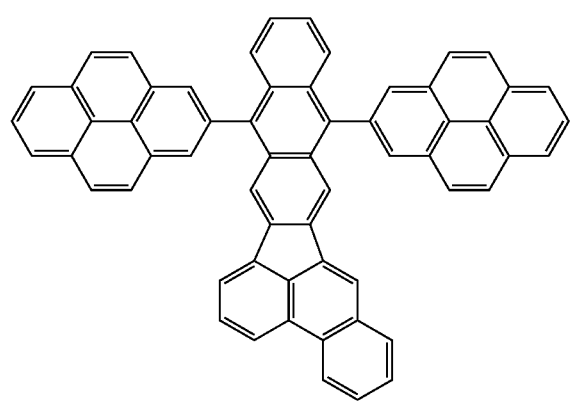
b-25

-continued
b-26
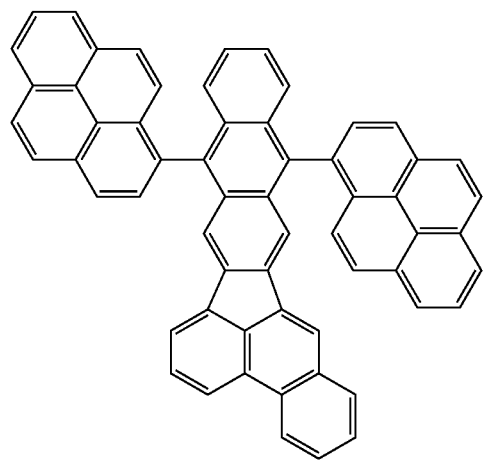
b-27
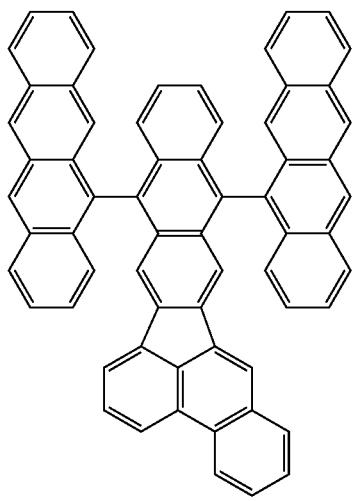
b-28
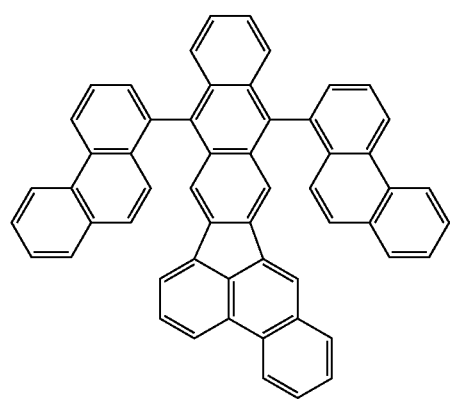
b-29
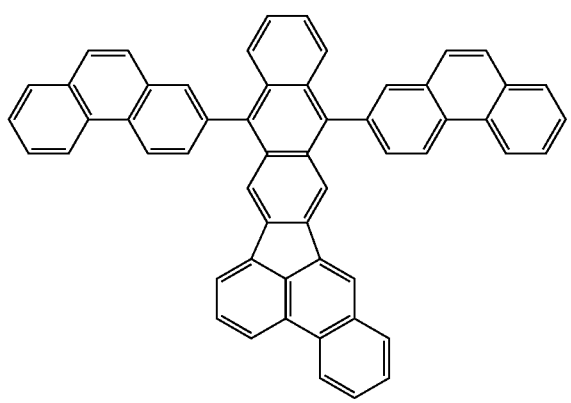
b-30
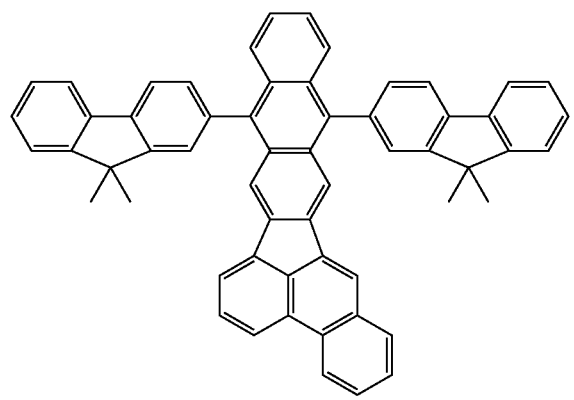
b-31
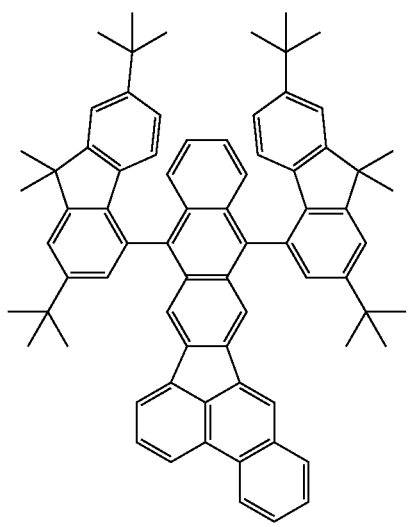

b-32
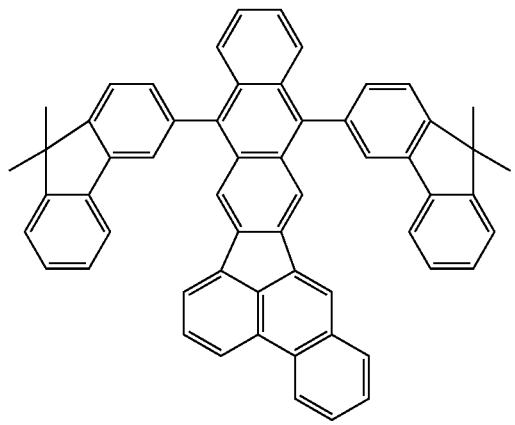
[Chem. 8]
b-33
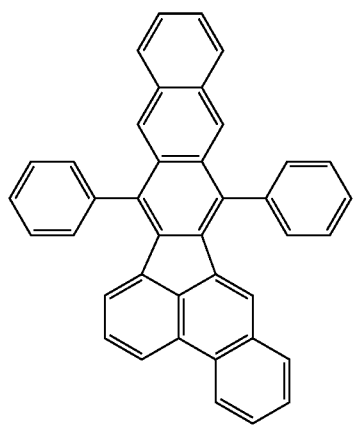
b-34
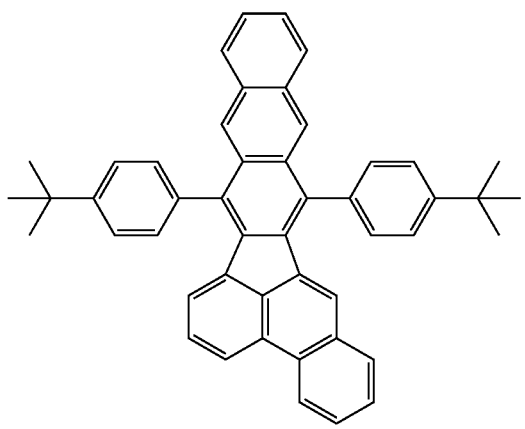
b-35
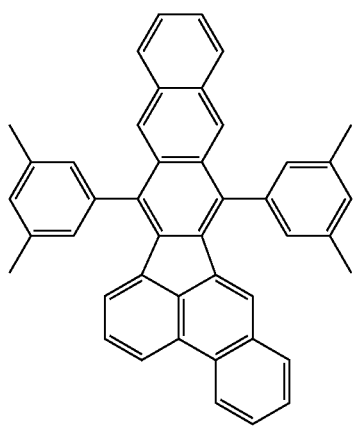
b-36
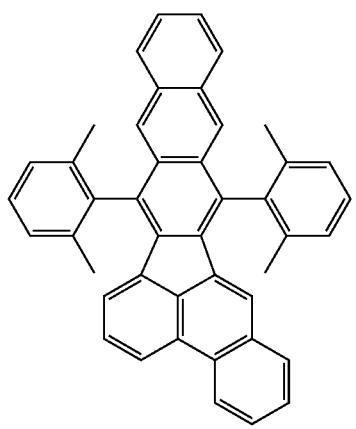

-continued
b-37
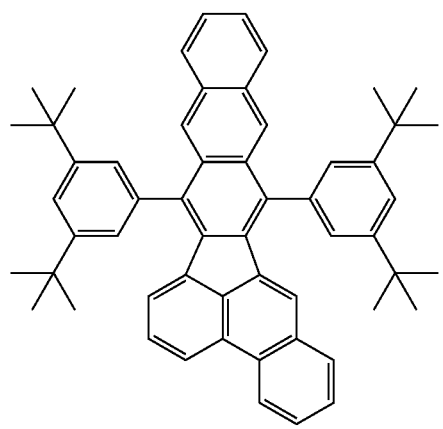
b-38
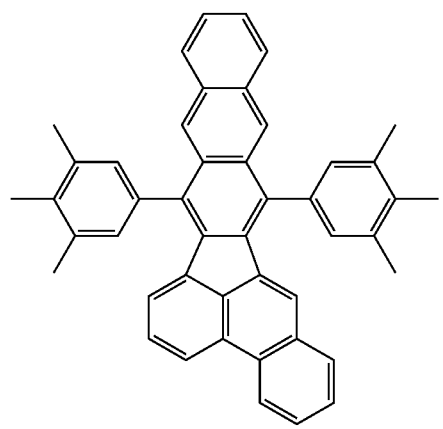
b-39
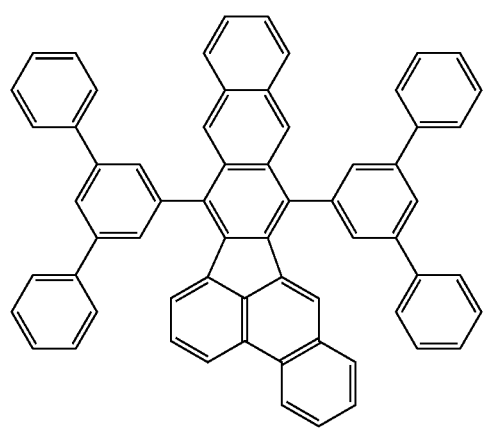
b-40
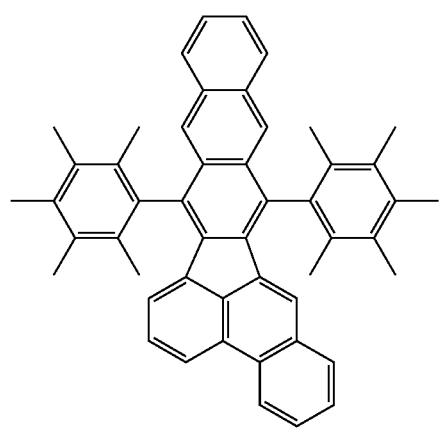
b-41
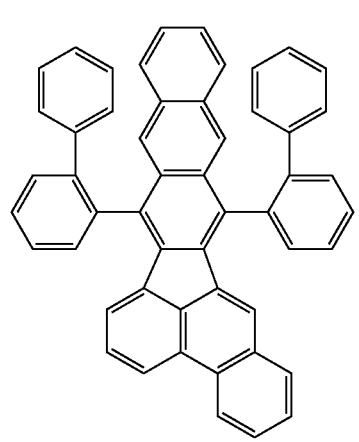
b-42
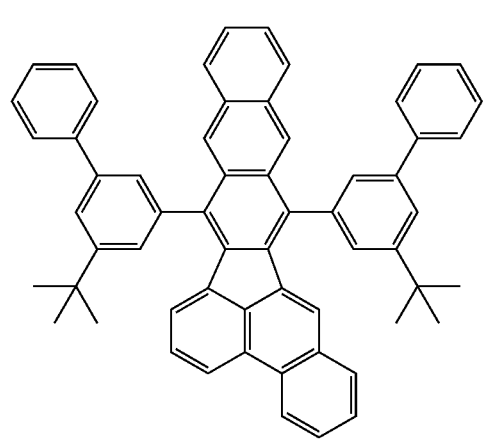

-continued
b-43
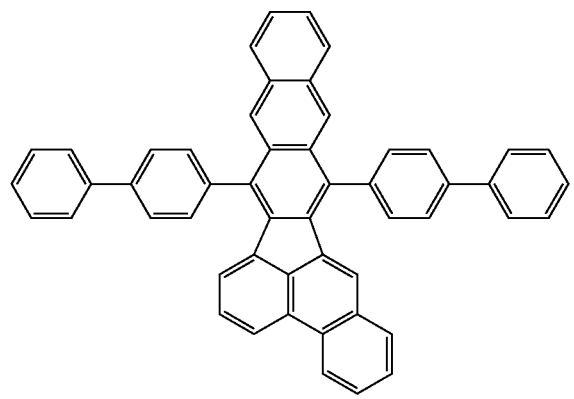
b-44
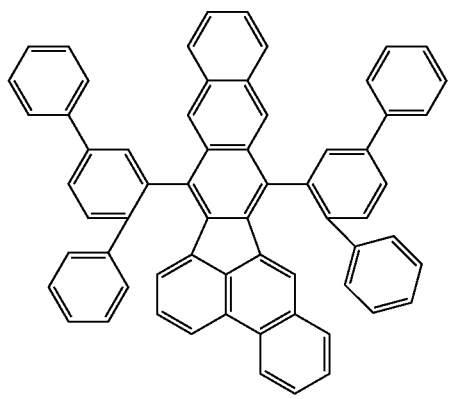
b-45
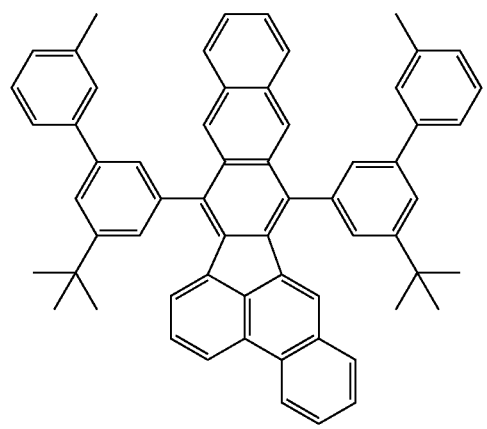
b-46
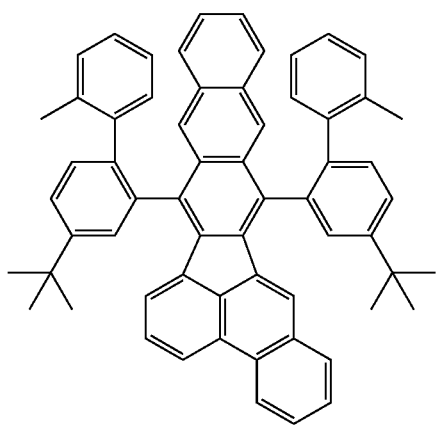
b-47
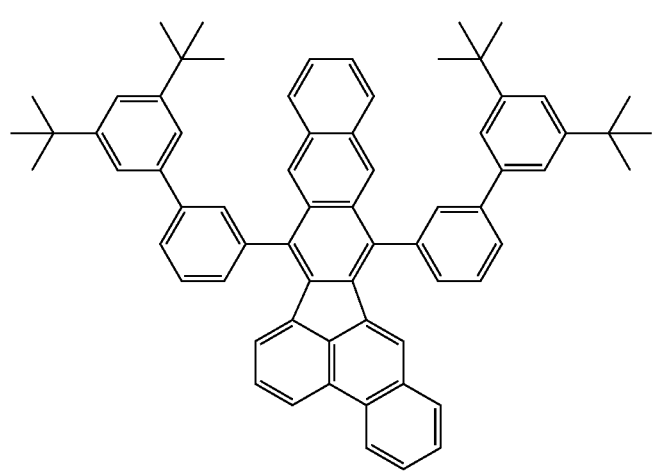

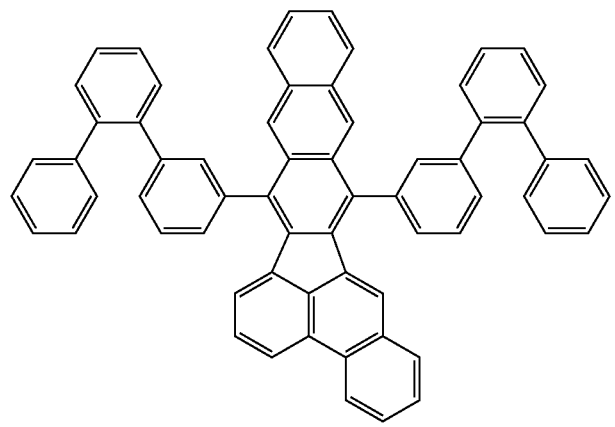
b-48
[Chem. 9]
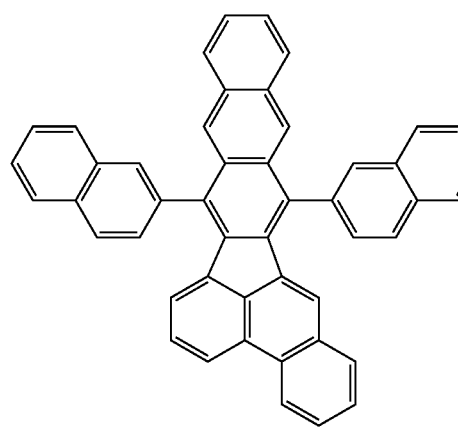
b-49
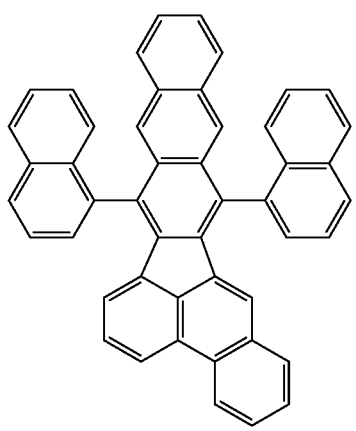
b-50
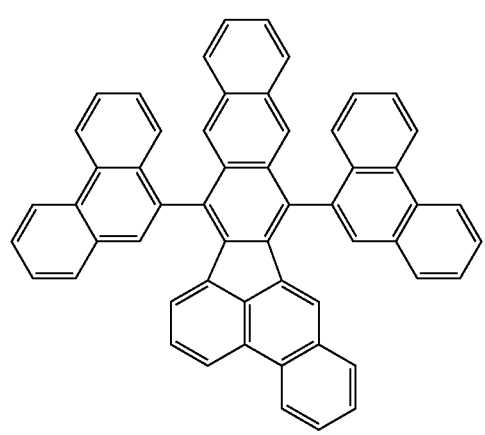
b-51
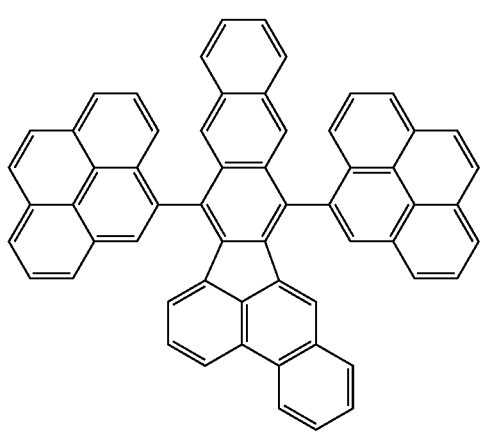
b-52

-continued
b-53
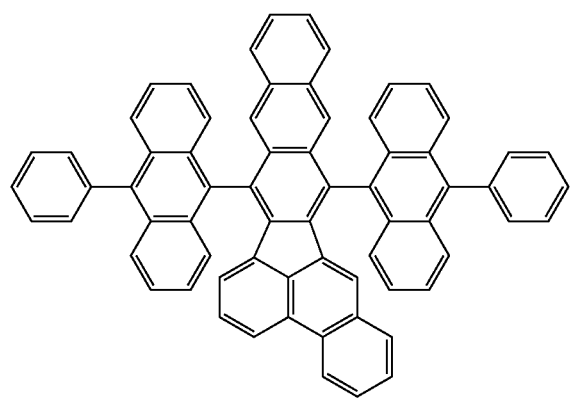
b-54
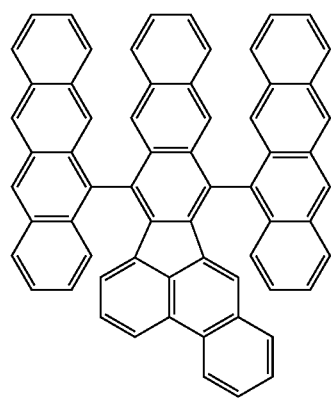
b-55
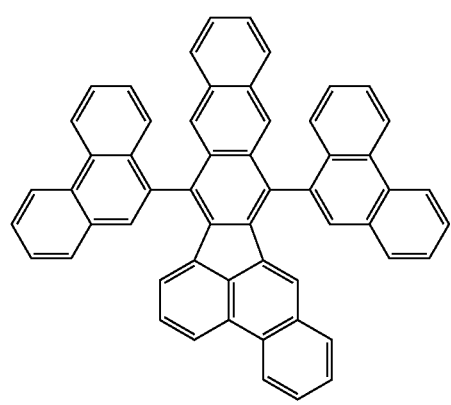
b-56
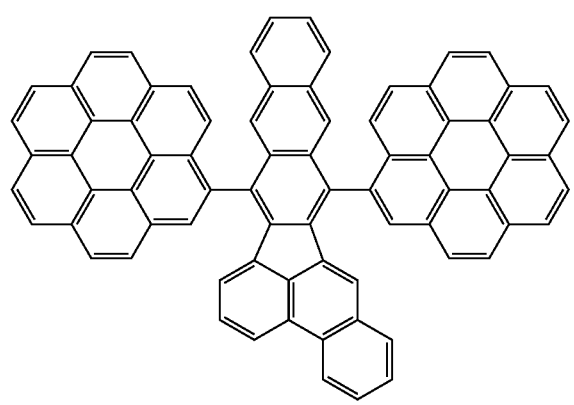
b-57
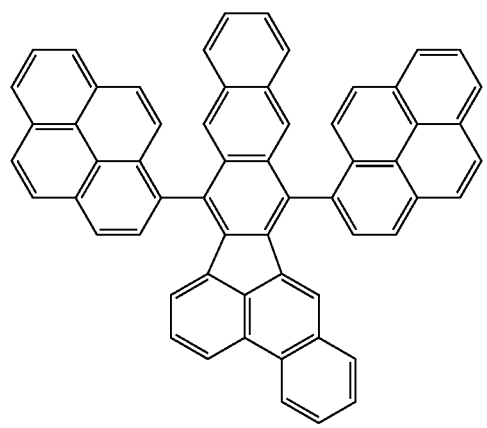
b-58
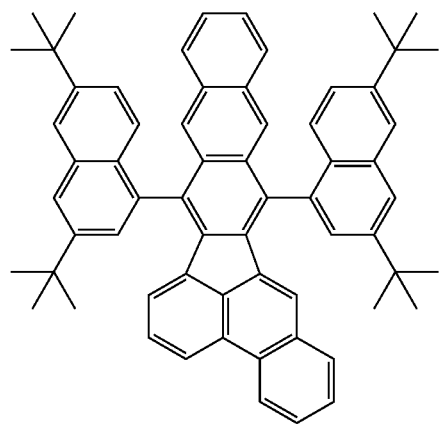

b-59
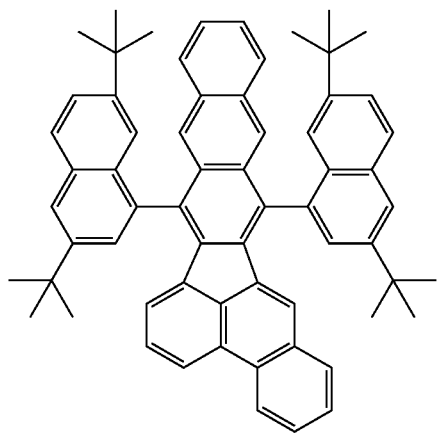
b-60
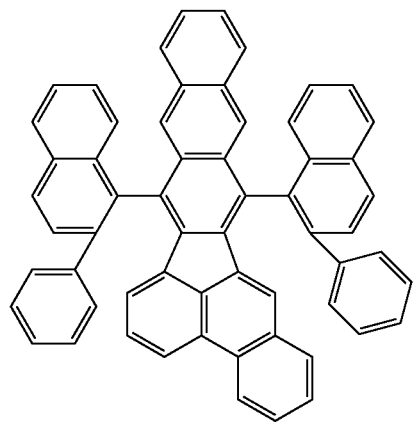
b-61
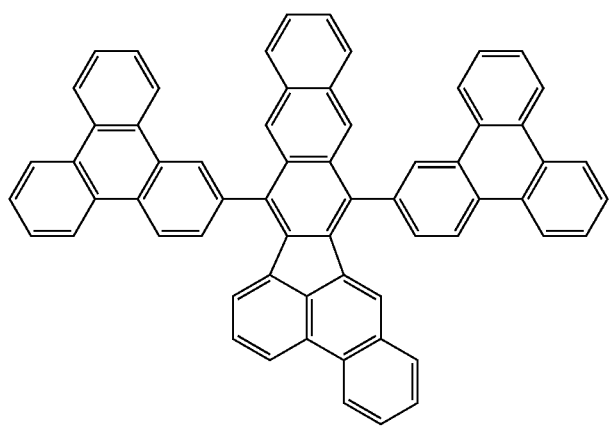
b-62
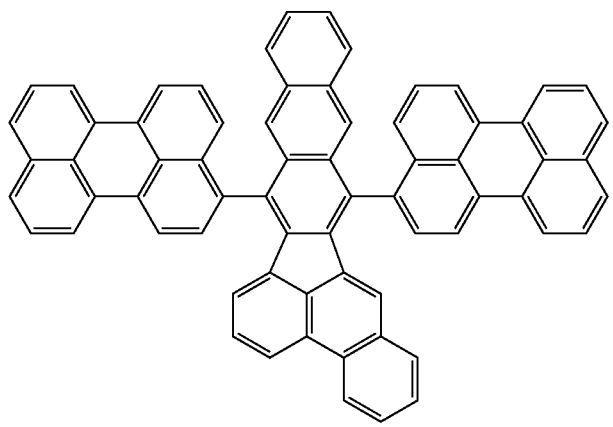

-continued
b-63
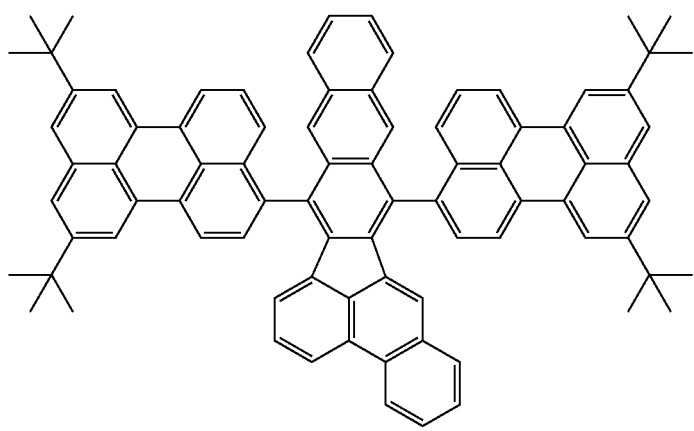
b-64
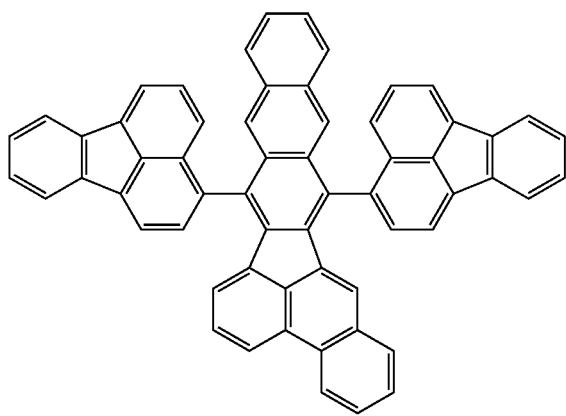
b-65
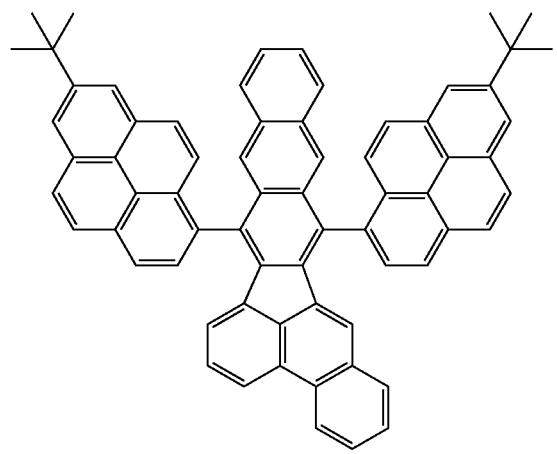
b-66
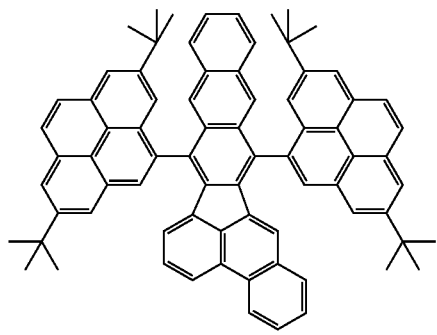
b-67
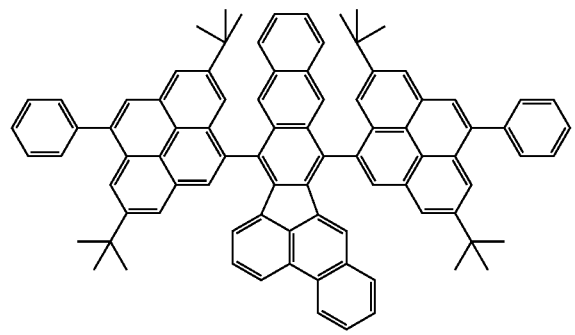

b-68
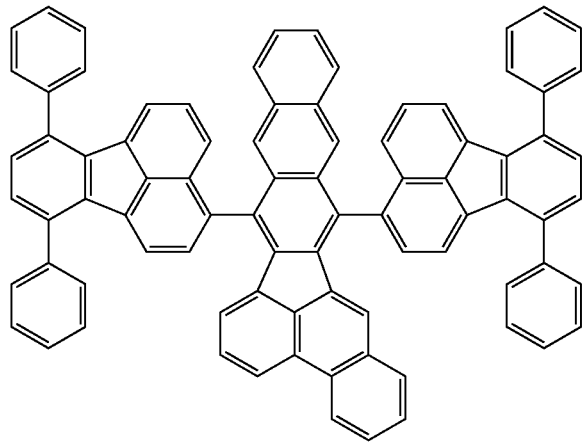
[Chem. 10]
b-69
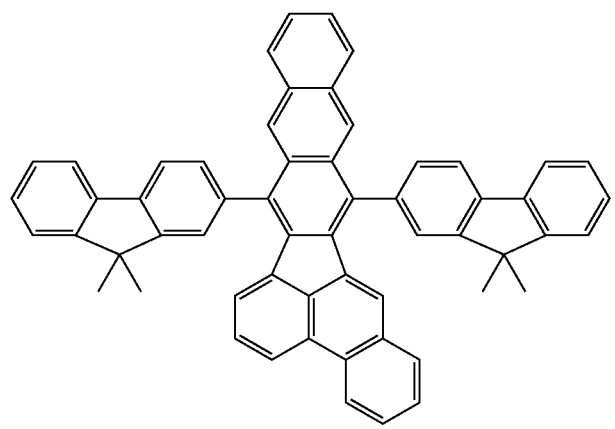
b-70
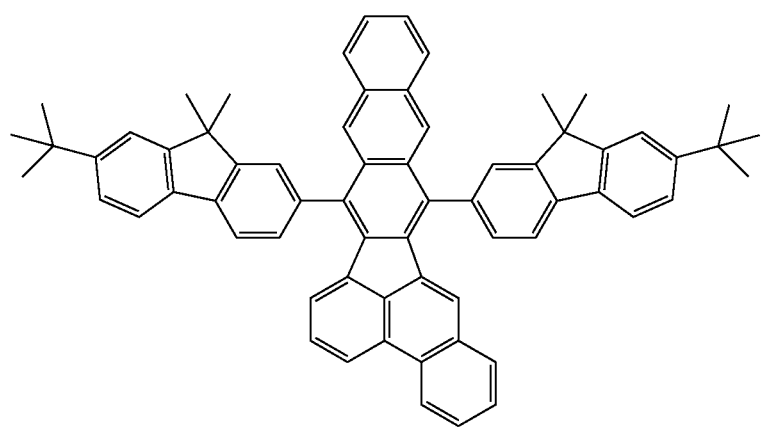

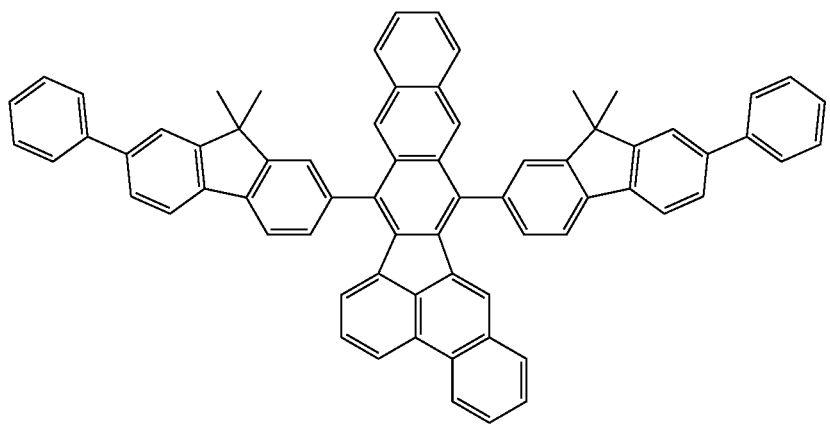
b-71
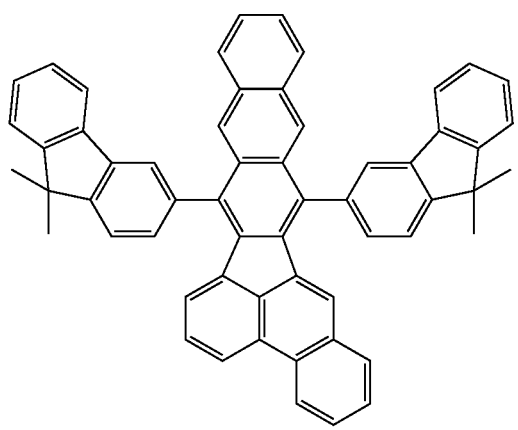
b-72
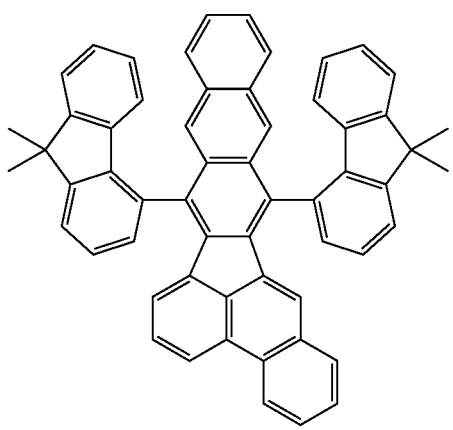
b-73
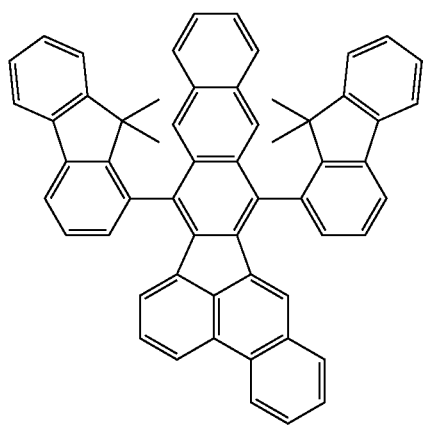
b-74
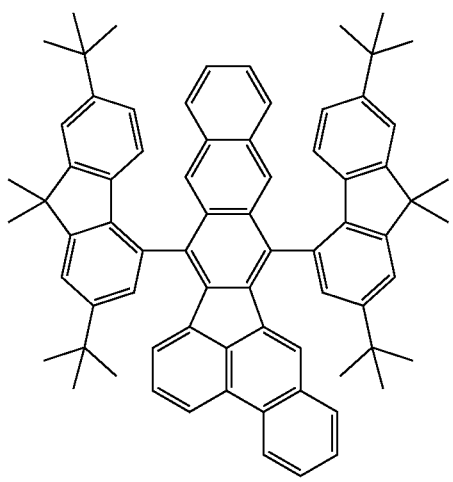
b-75

-continued
b-76
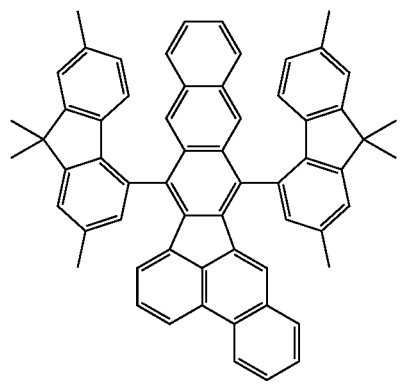
b-77
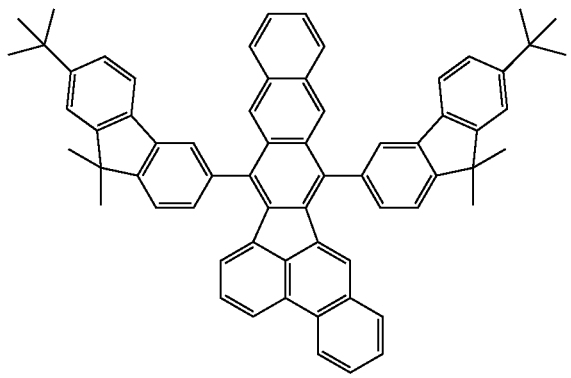
[Chem. 11]
b-78
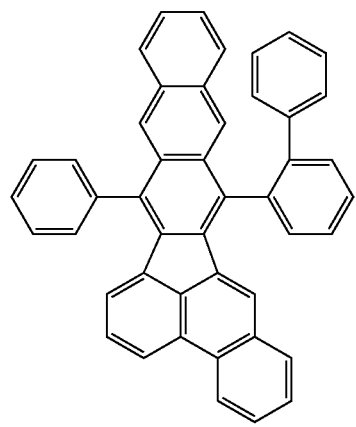
b-79
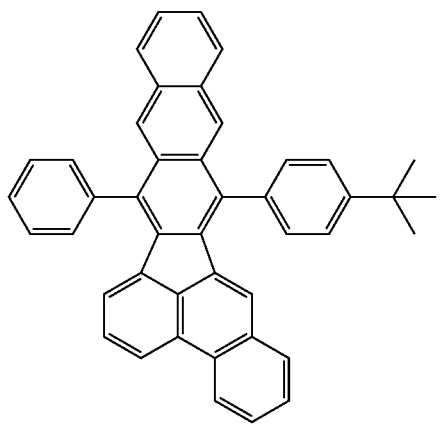
b-80
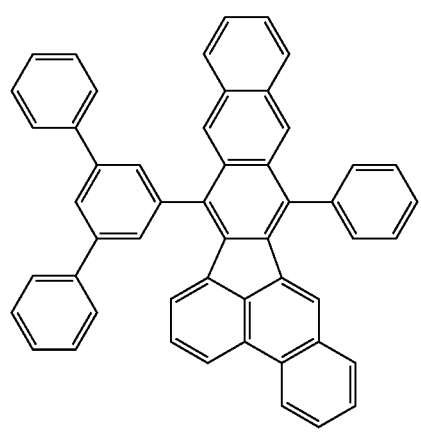
b-81
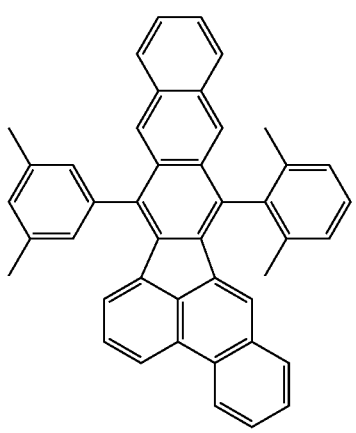

-continued
b-82
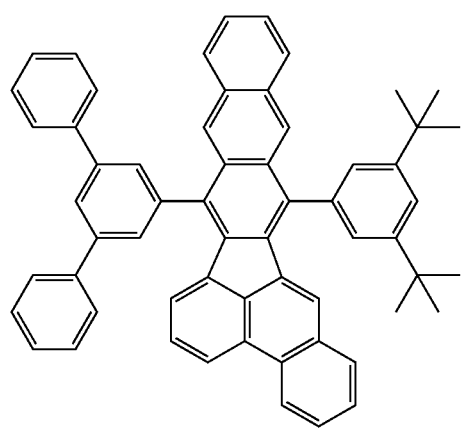
b-83
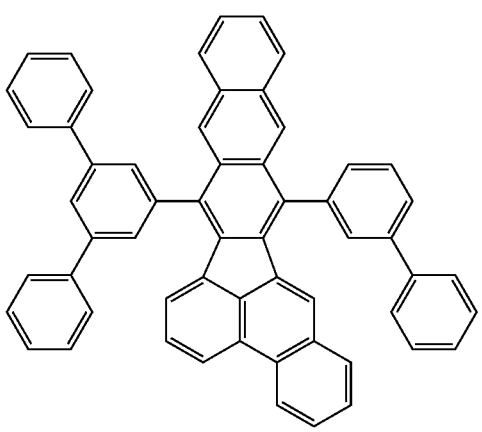
b-84
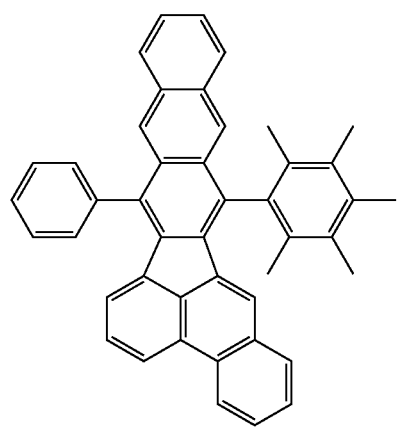
b-85
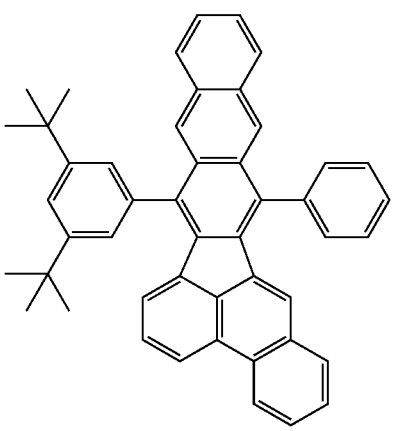
b-6
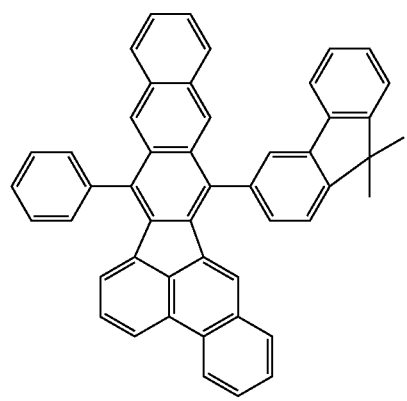
b-87
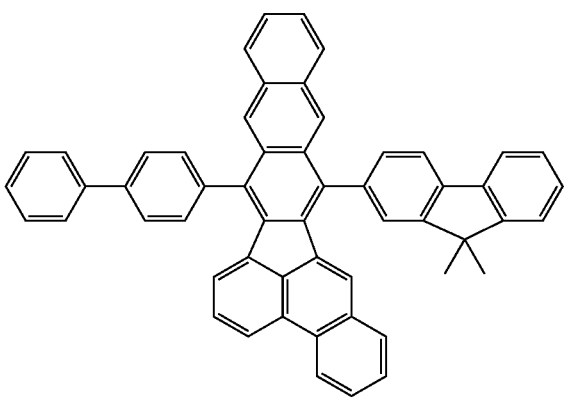

-continued
b-80
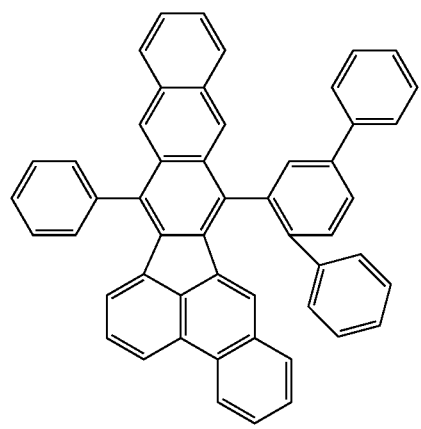
b-89
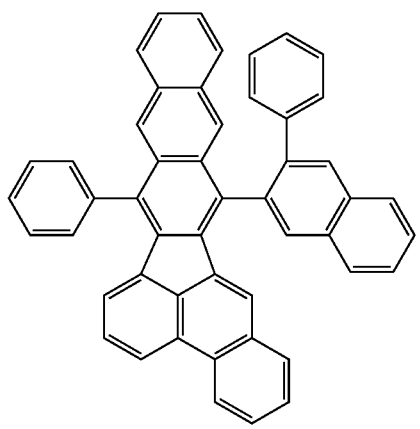
b-91
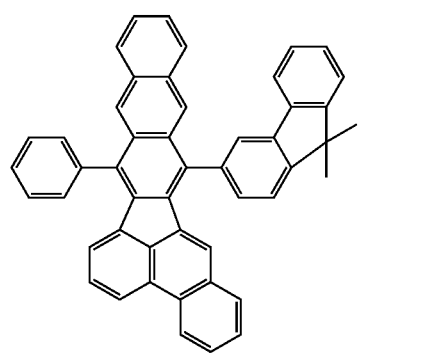
b-92
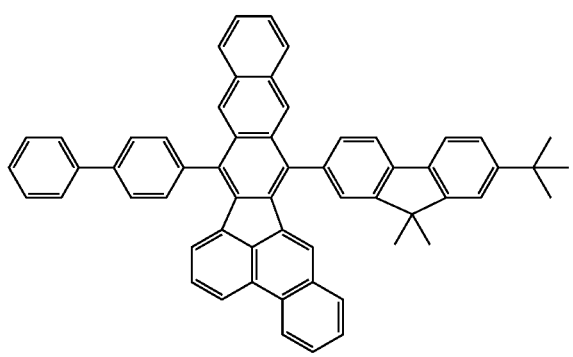
b-93
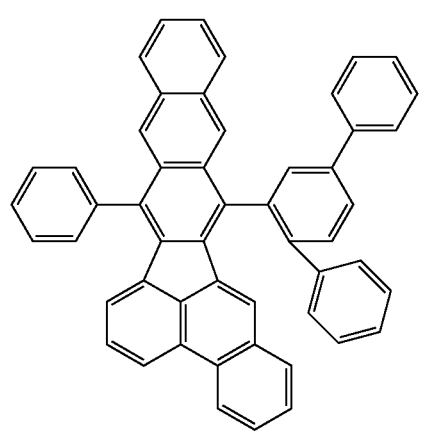
b-94
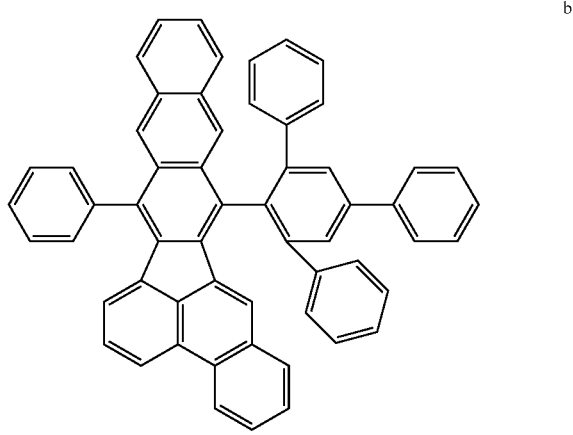
b-95
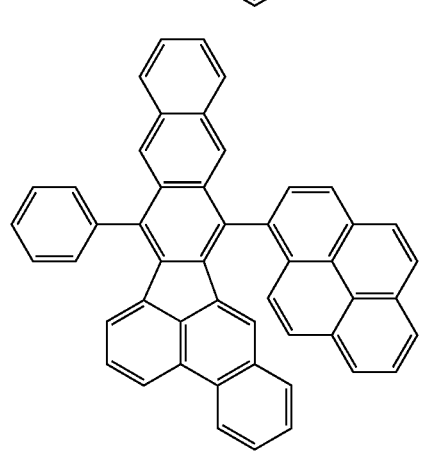
b-96
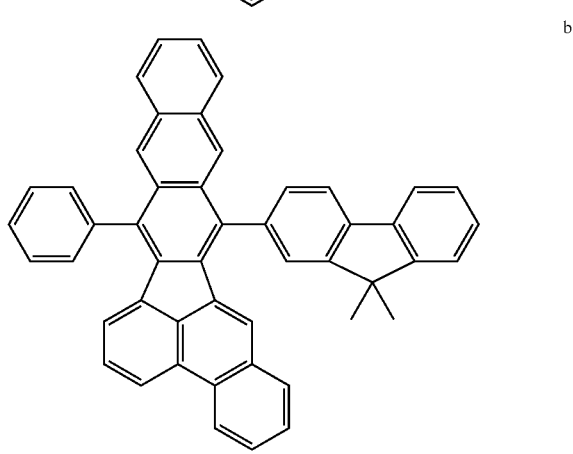

-continued
b-97
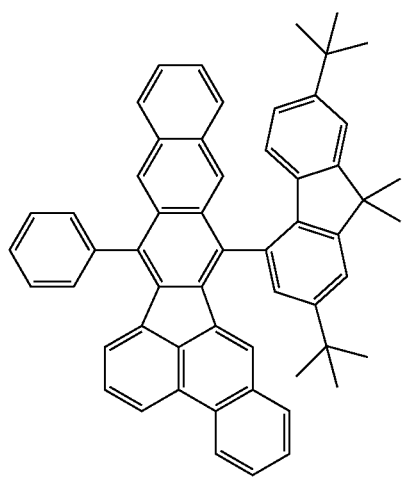
b-98
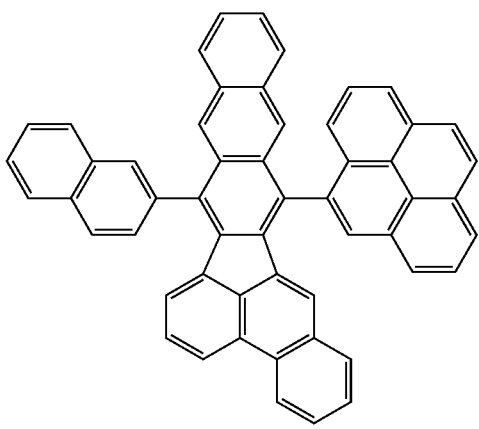
[Chem. 12]
c-1
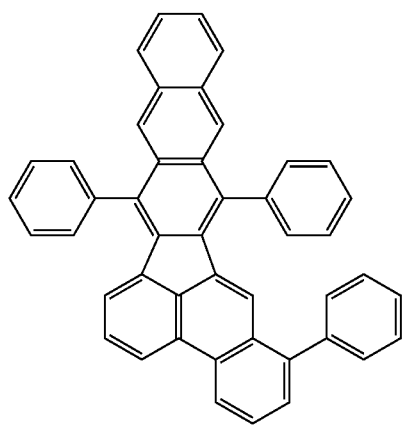
c-2
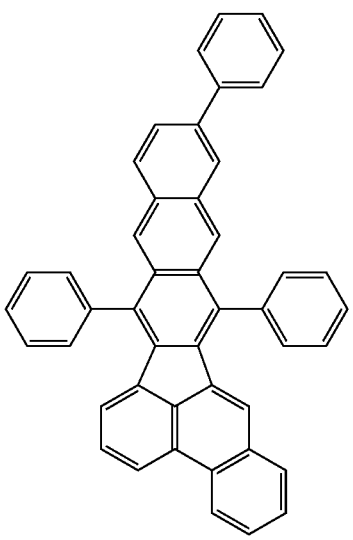
c-3
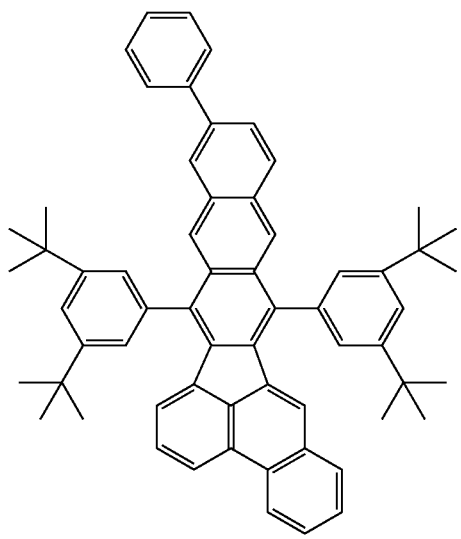
c-4
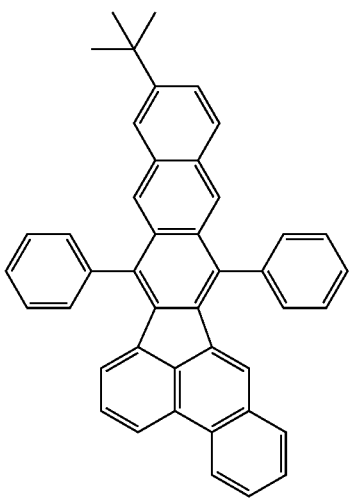

-continued
c-5
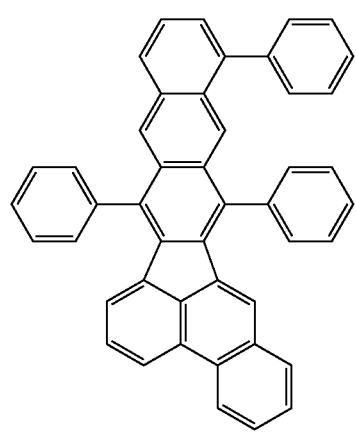
c-6
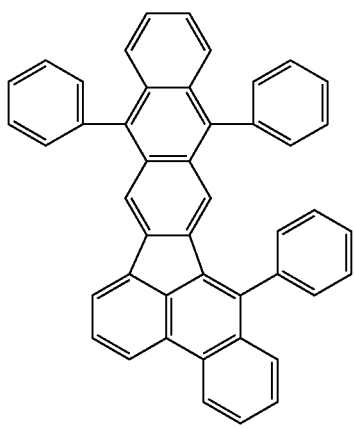
c-7
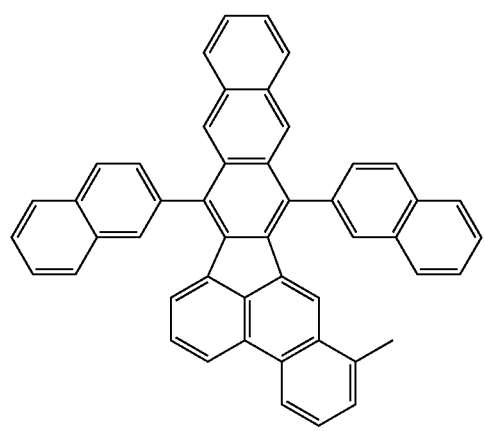
c-8
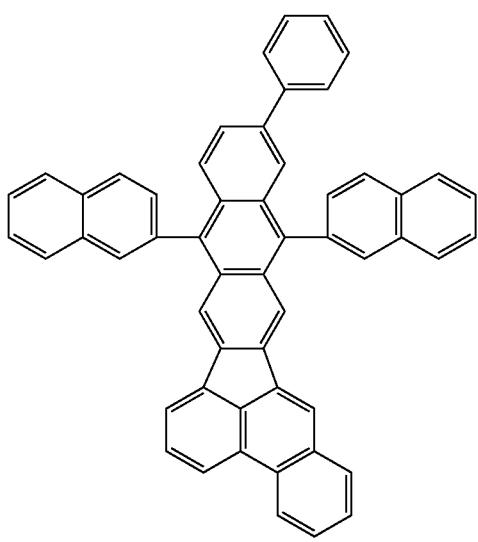
c-9
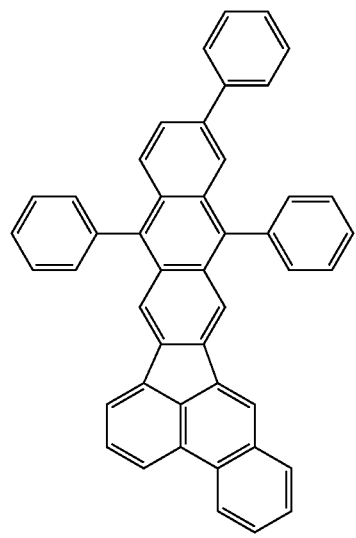
c-10
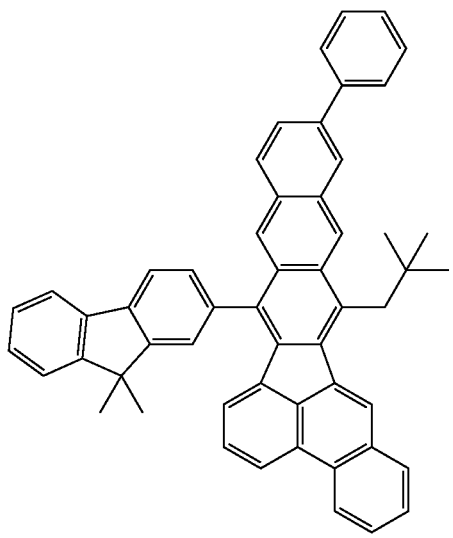

-continued
c-11
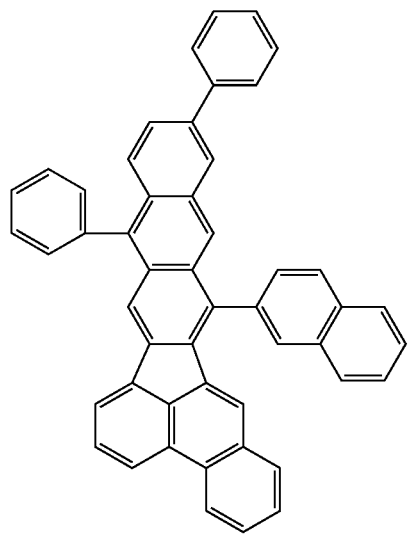
c-12
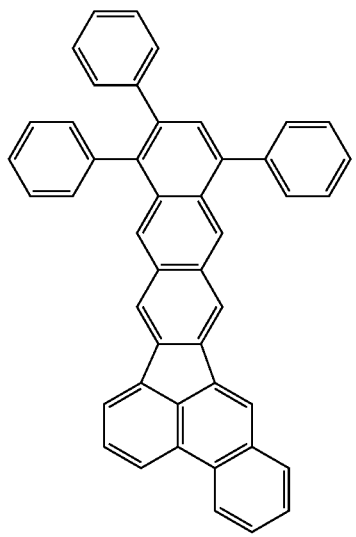
[Chem. 13]
d-1
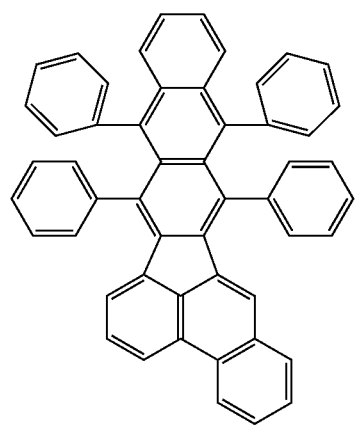
d-2
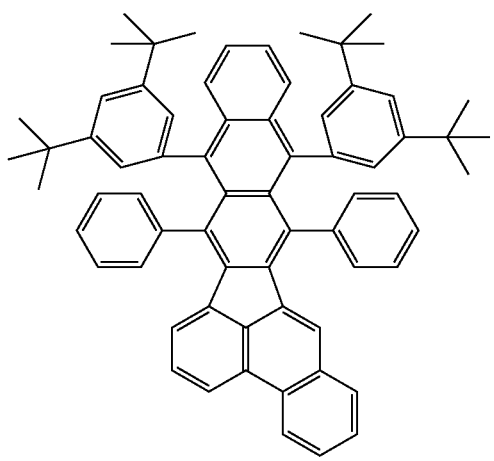
d-3
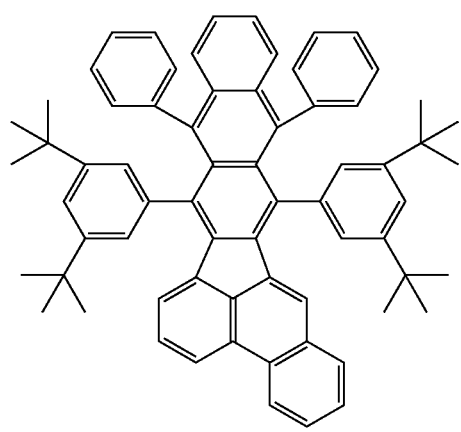
d-4
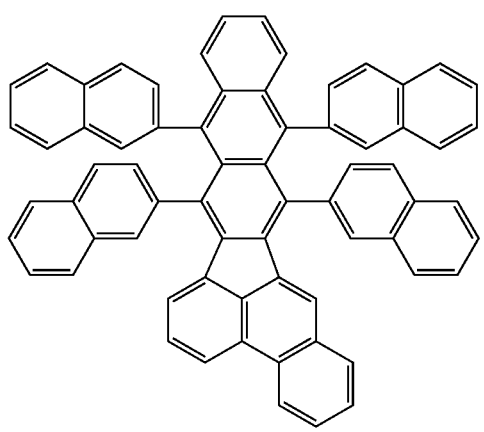

-continued
d-5
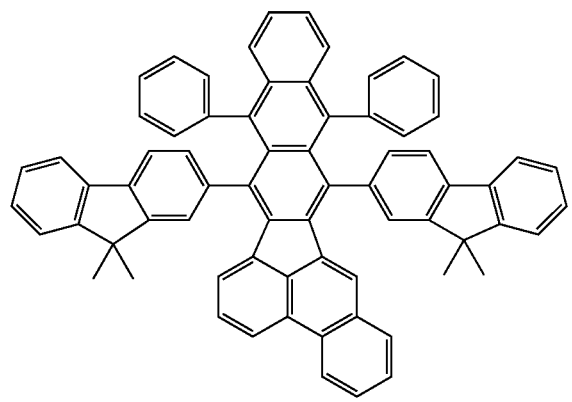
d-6
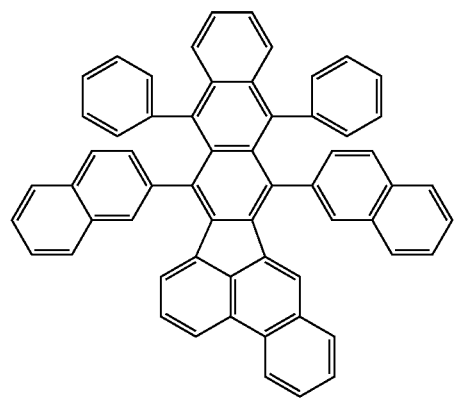
d-7
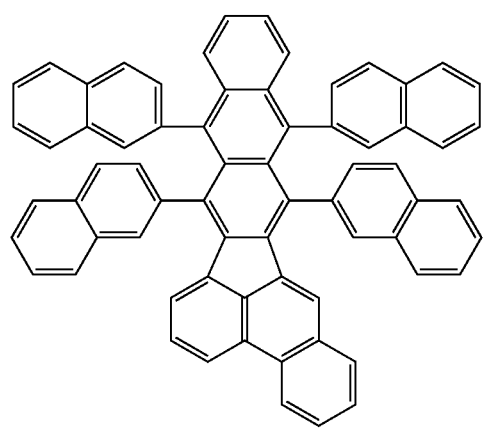
d-8
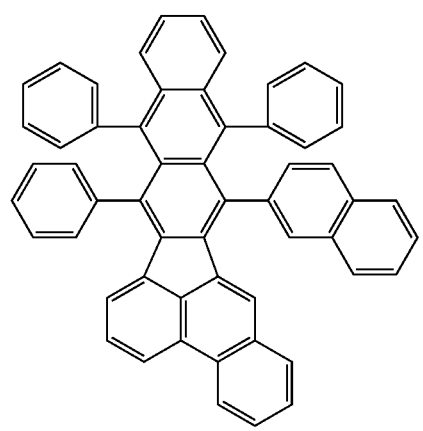
d-9
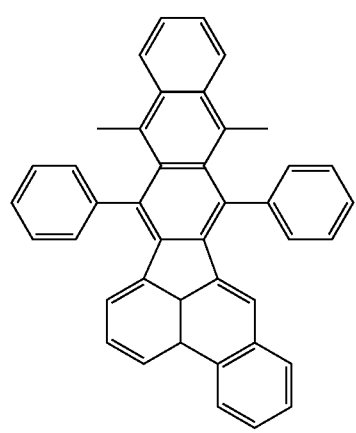
d-10
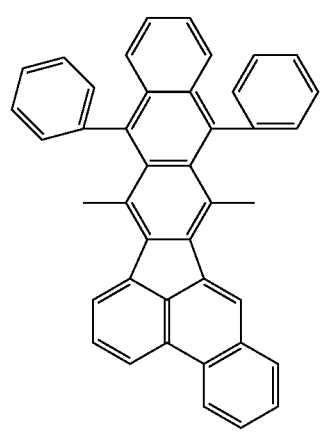

-continued
d-11
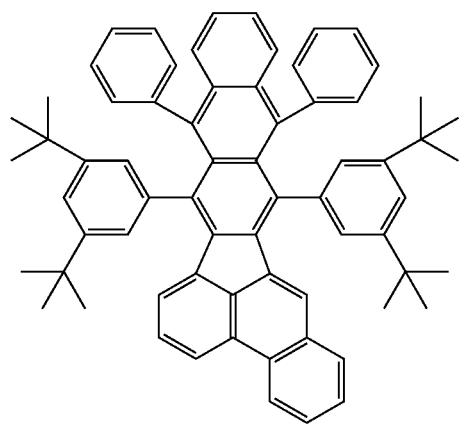
d-12
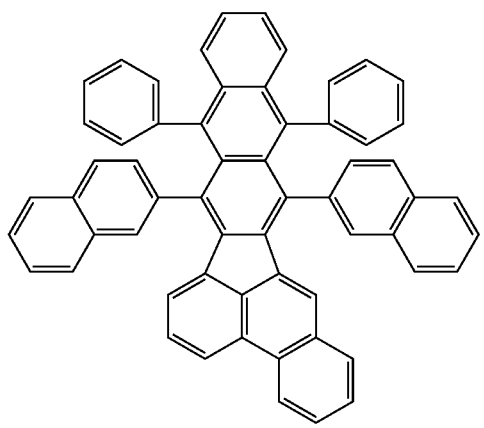
d-13
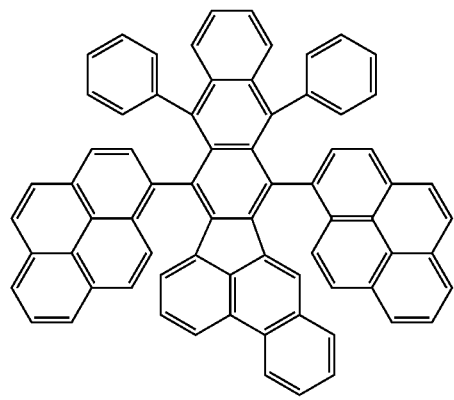
d-14
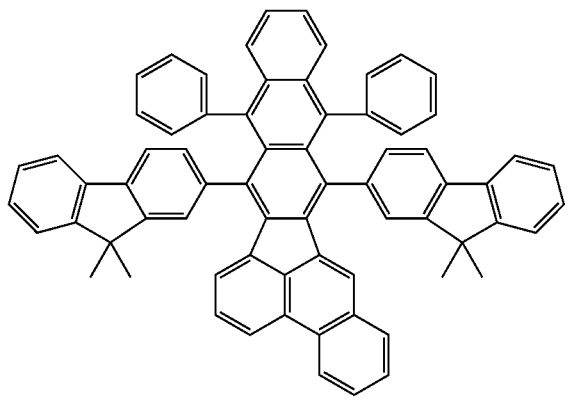
d-15
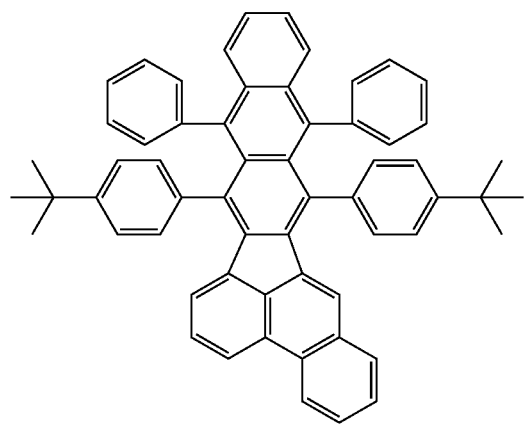
d-16
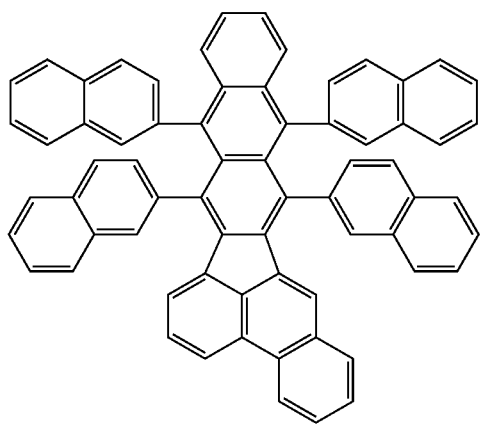

[Chem. 14]
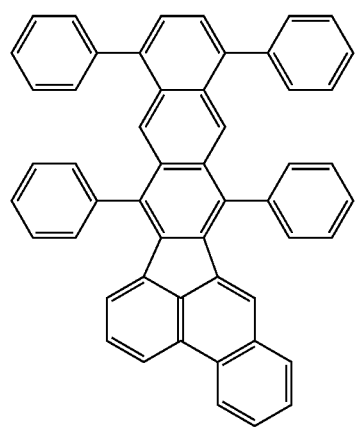
d-17
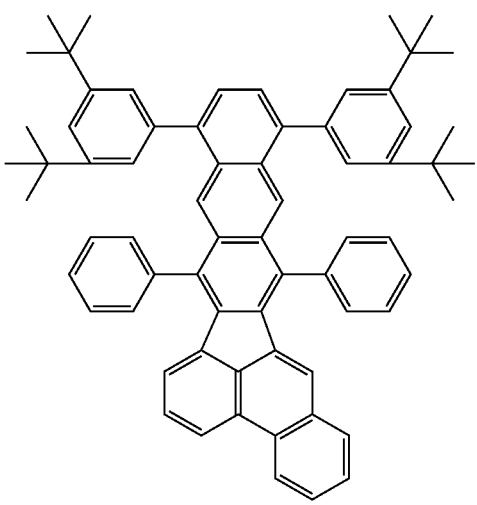
d-18
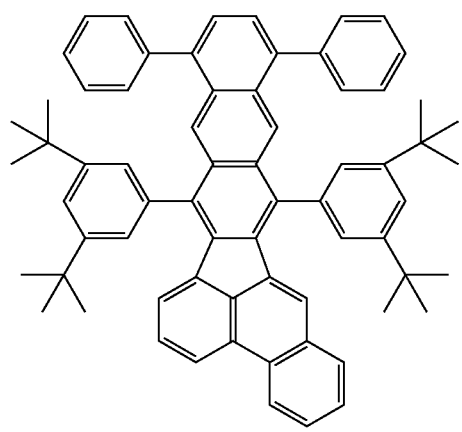
d-19
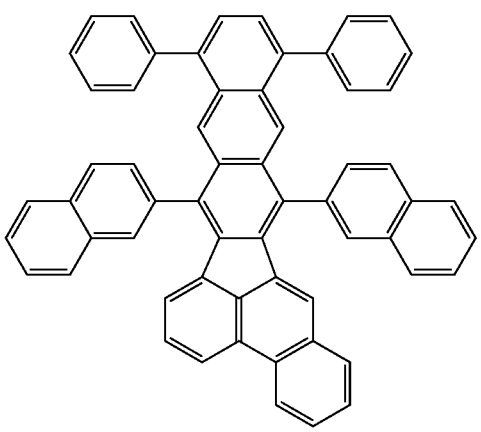
d-20
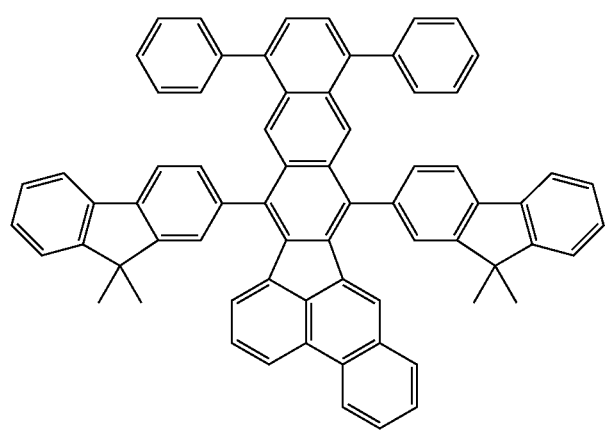
d-17

-continued
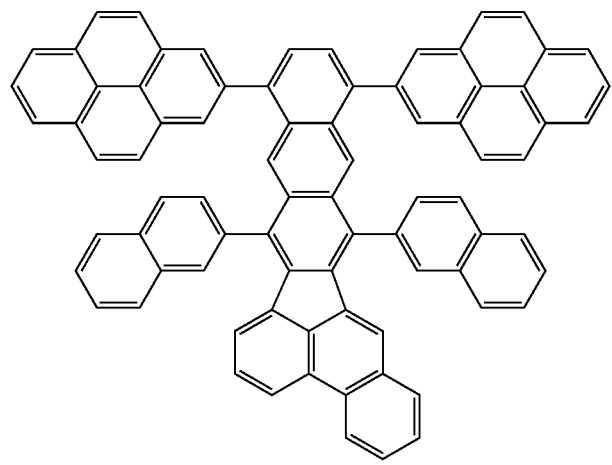
d-18
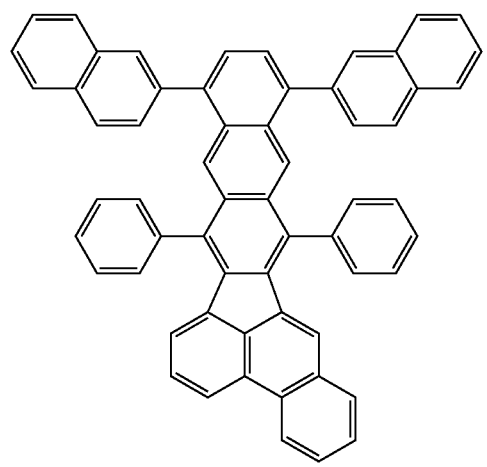
d-19
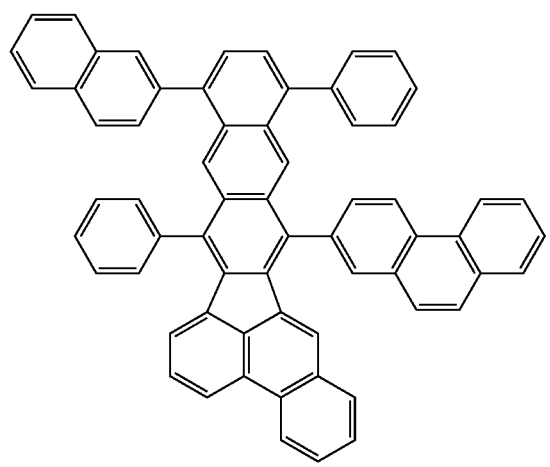
d-20
[Chem. 15]
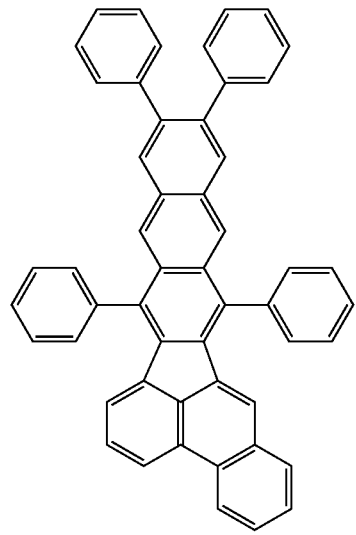
d-21
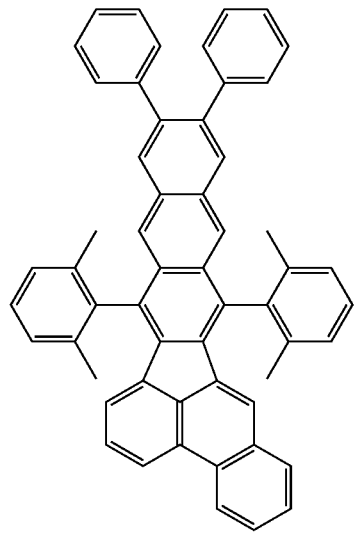
d-22

-continued
d-23
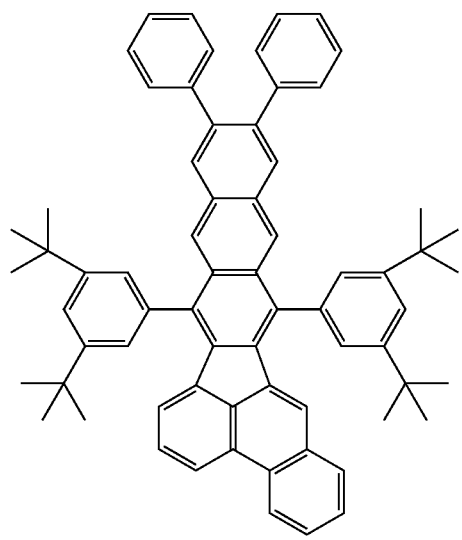
d-24
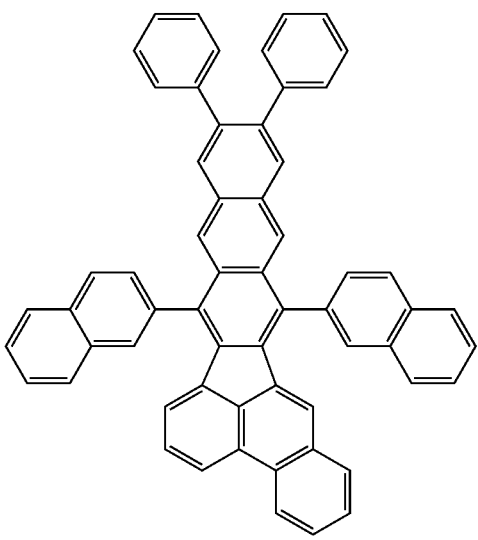
d-25
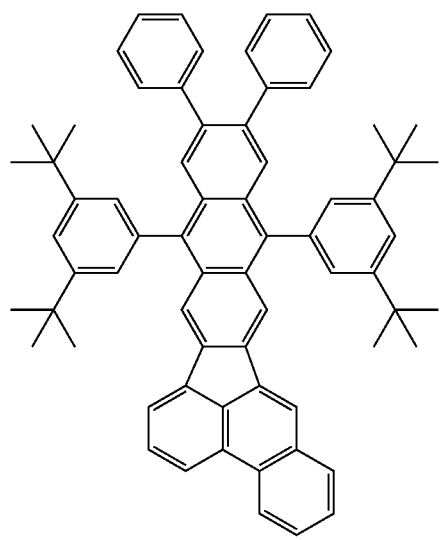
d-26
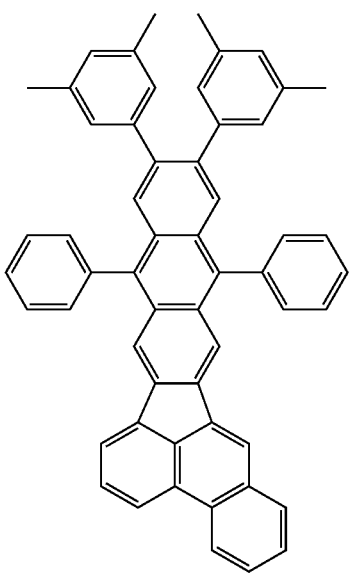
d-27
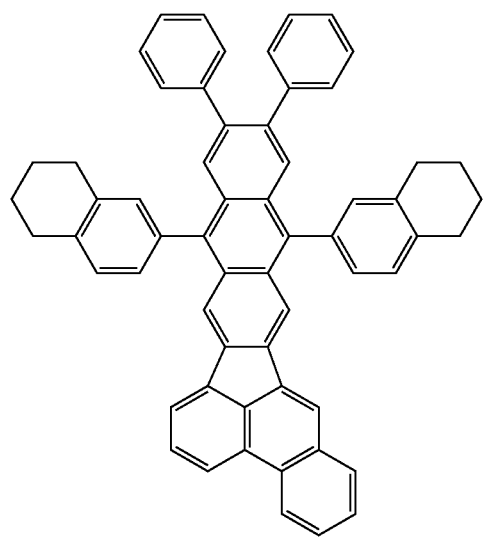
d-28
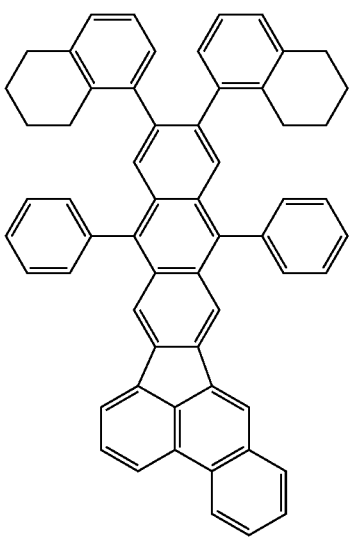

-continued
d-29
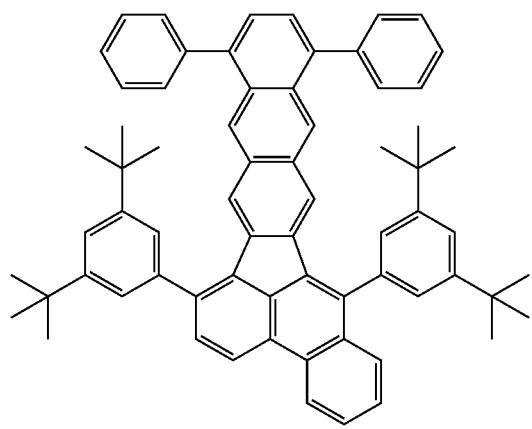
d-30
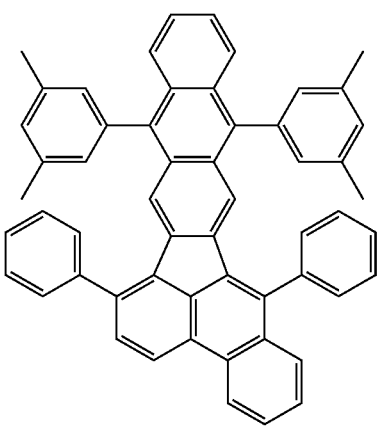
d-31
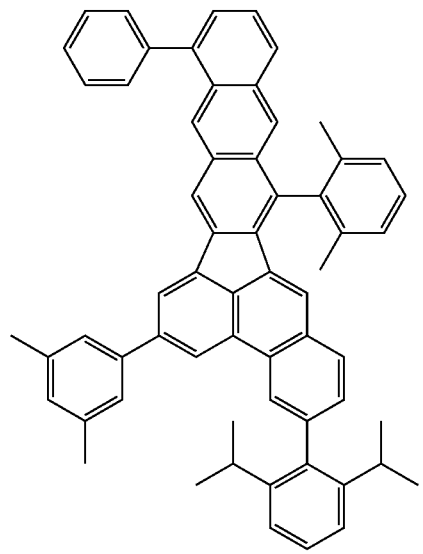
d-32
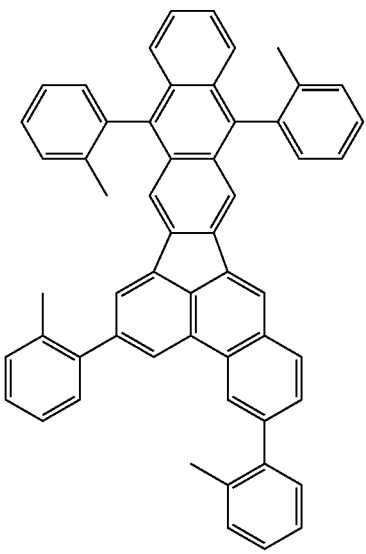
d-33
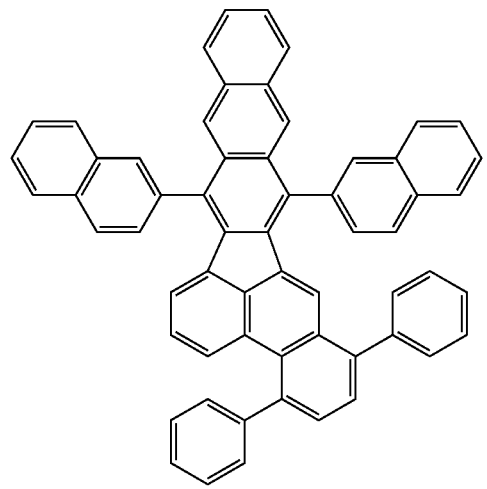
d-34
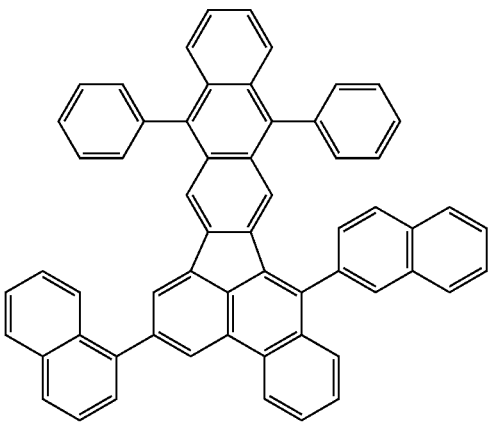

-continued
d-35
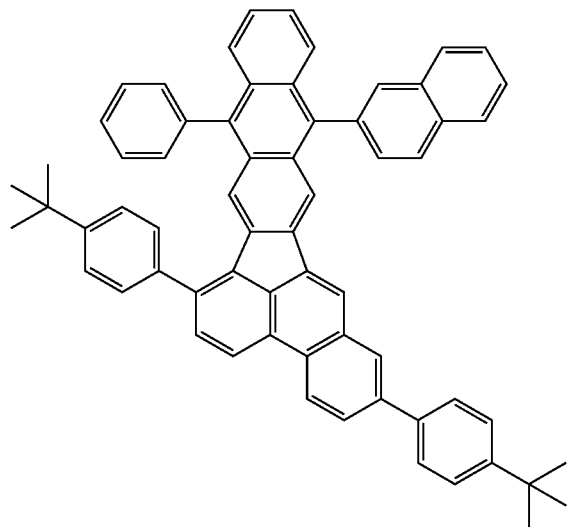
d-36
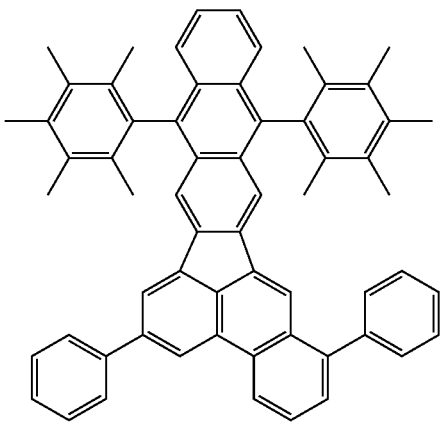
[Chem. 16]
e-1
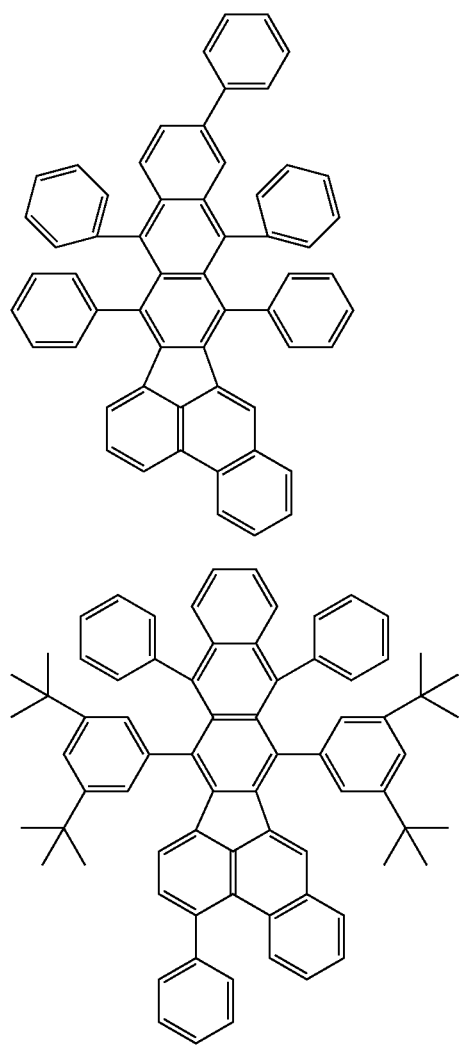
e-2
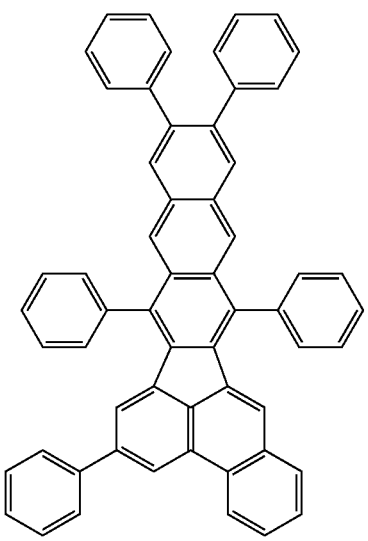
e-3
e-4
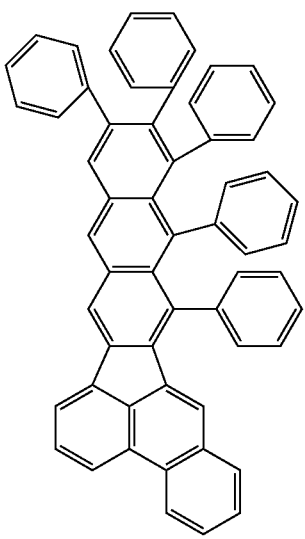

-continued
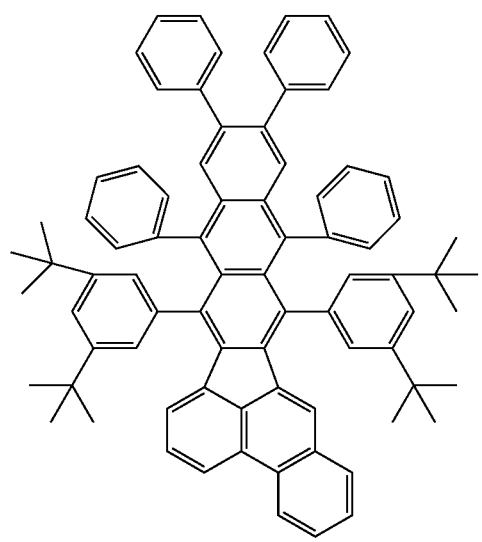
f-1
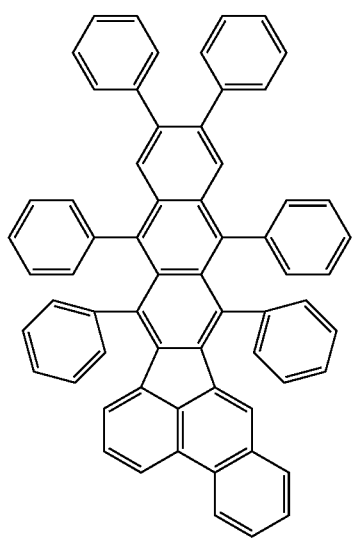
f-2
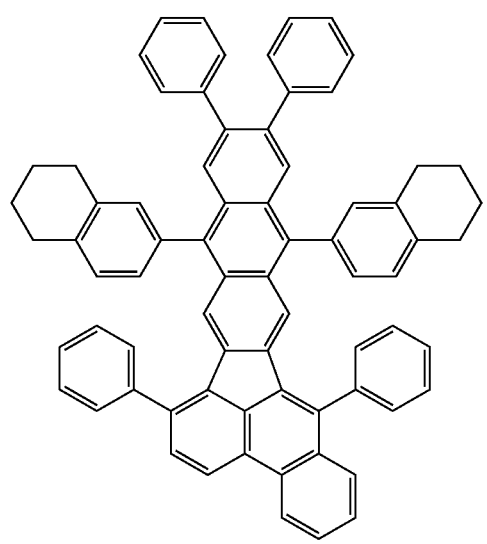
f-3
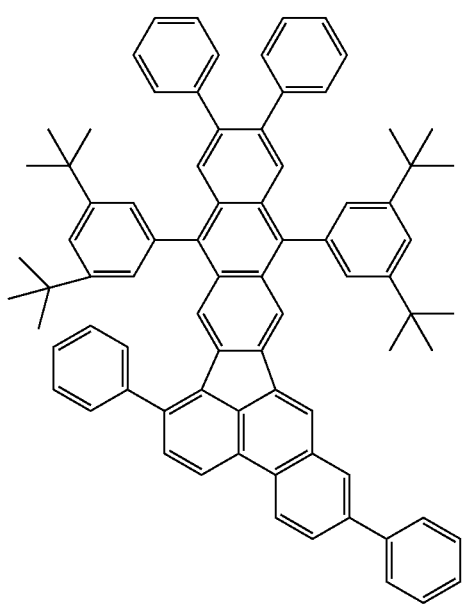
f-4

-continued
g-1
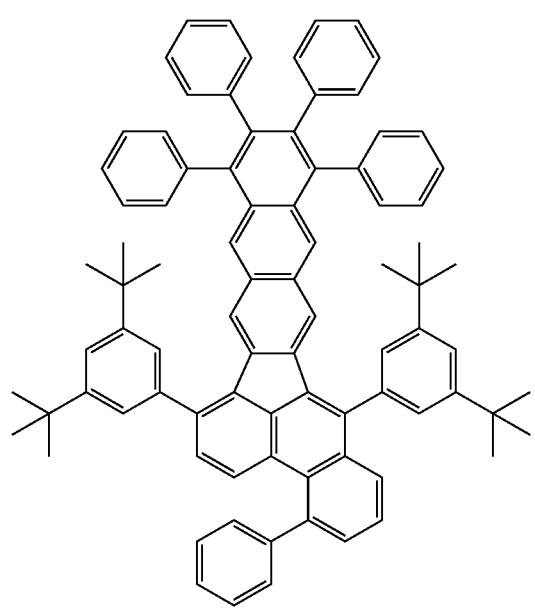
h-1
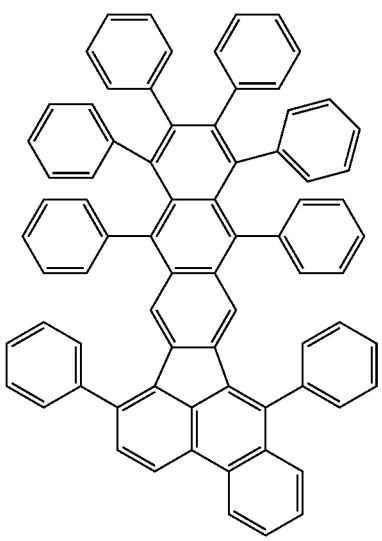
i-1
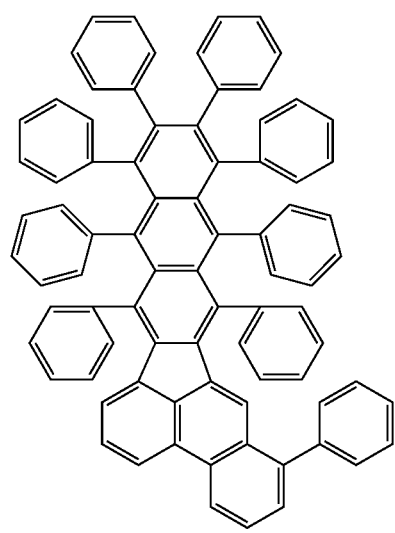
j-1
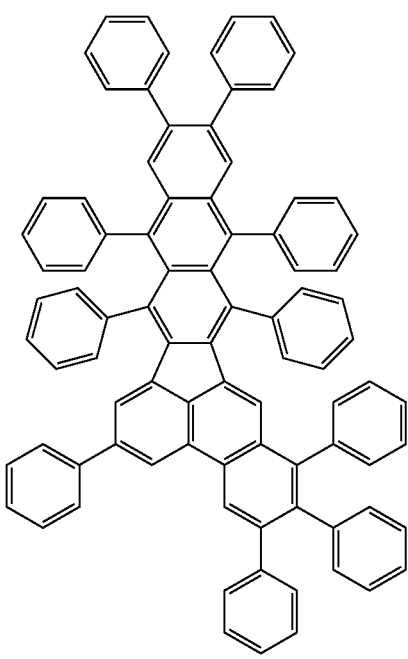

[Chem. 17]
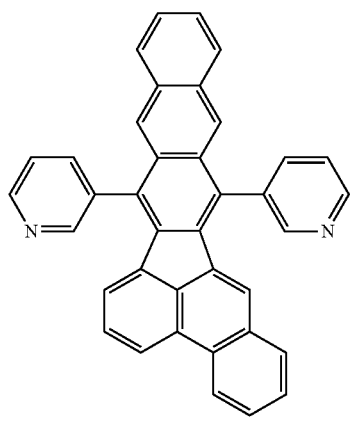
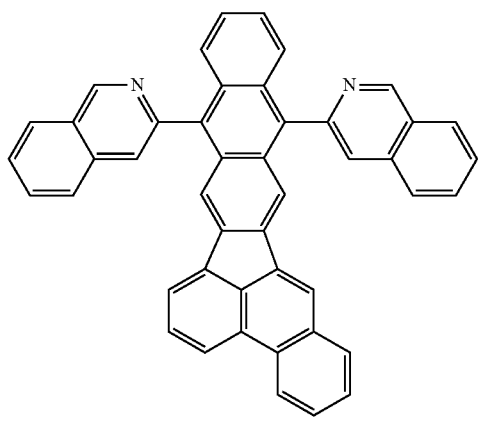
k-1        k-2
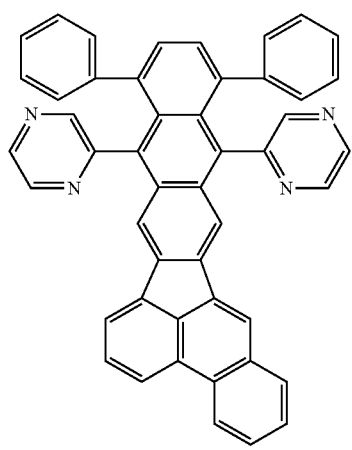
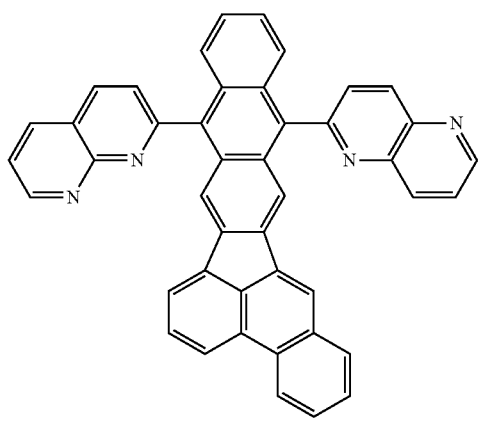
k-3        k-4
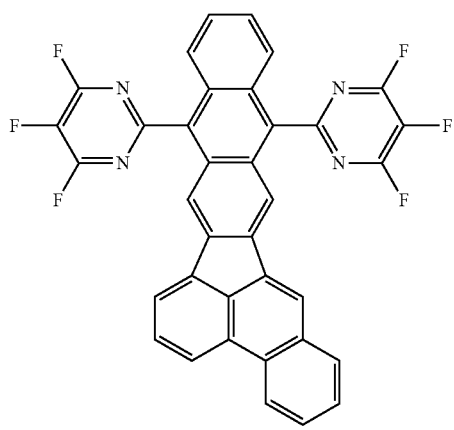
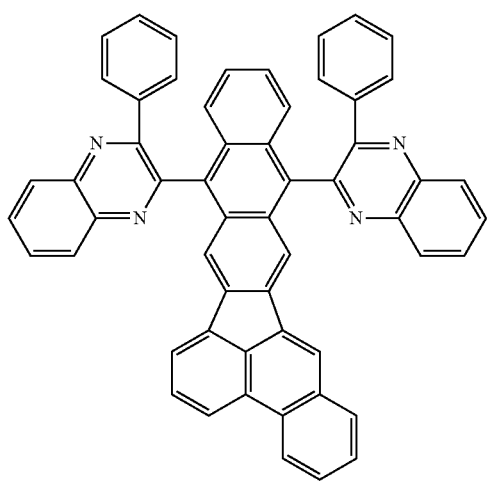
k-5        k-6

-continued
k-7
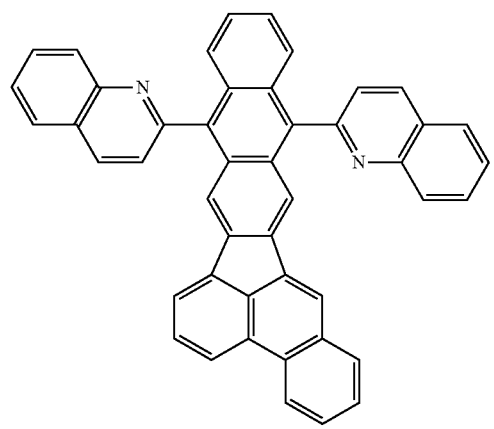
k-8
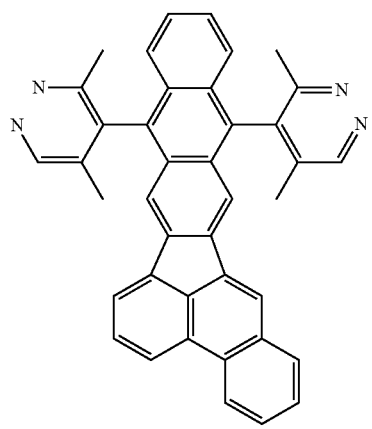
k-9
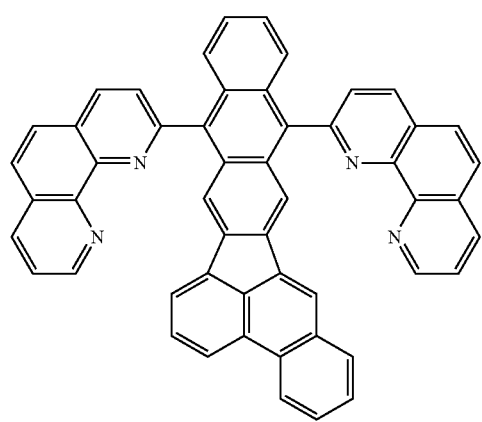
k-10
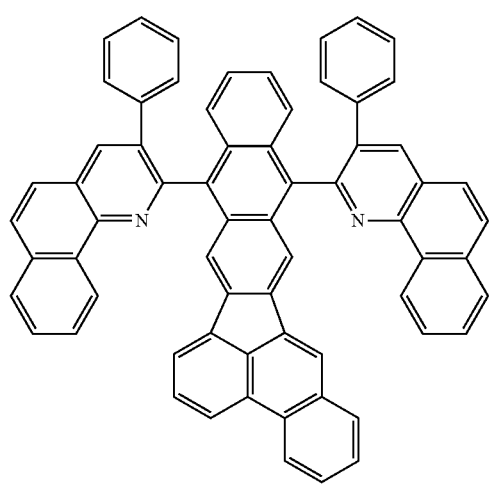
k-11
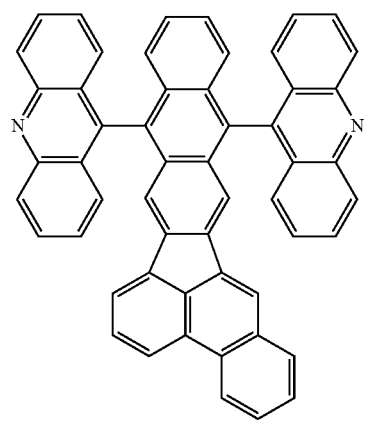
k-12
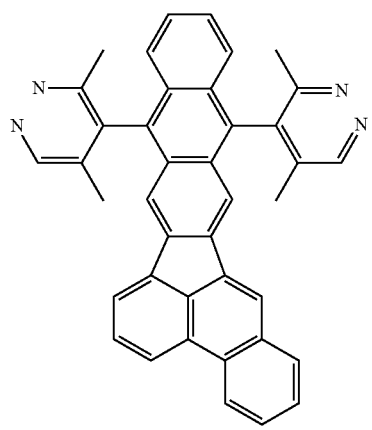

-continued
k-13
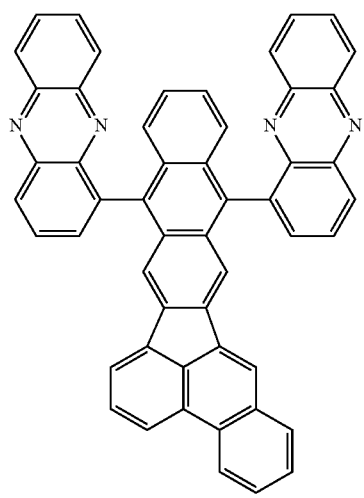
k-14
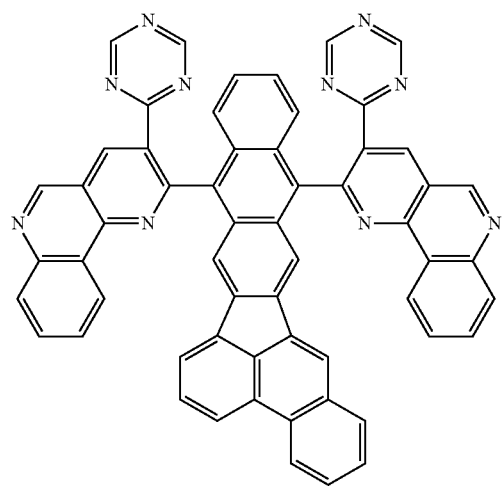
k-15
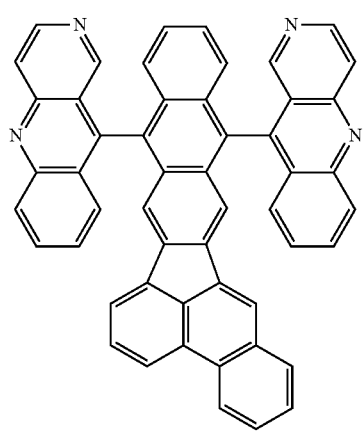
k-16
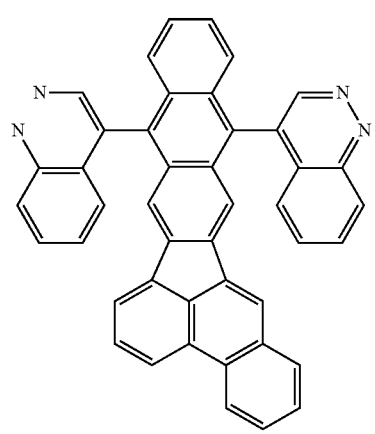
k-17
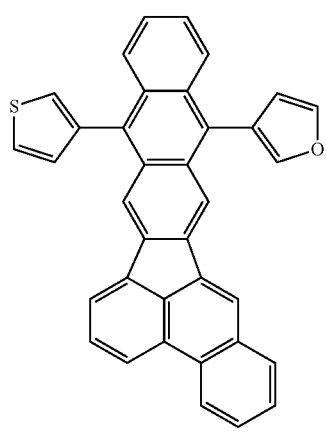
k-18
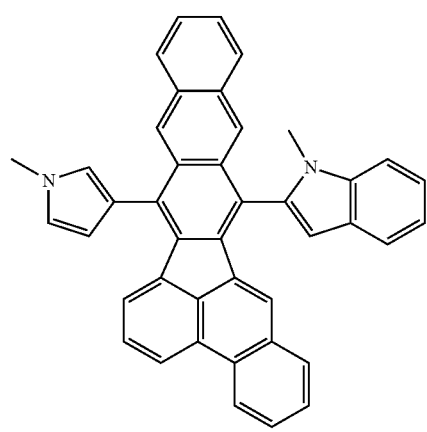

-continued
k-19
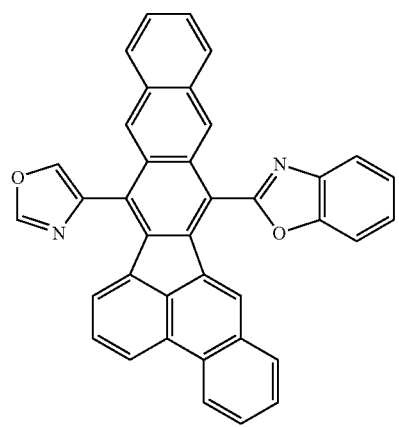
k-20
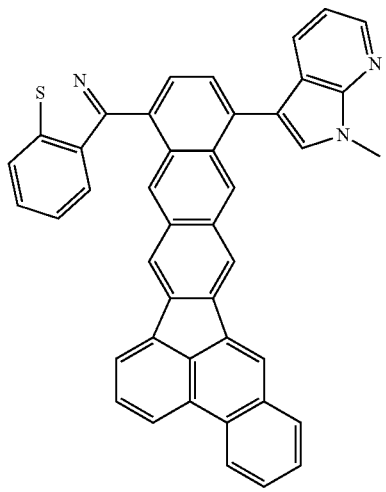
k-21
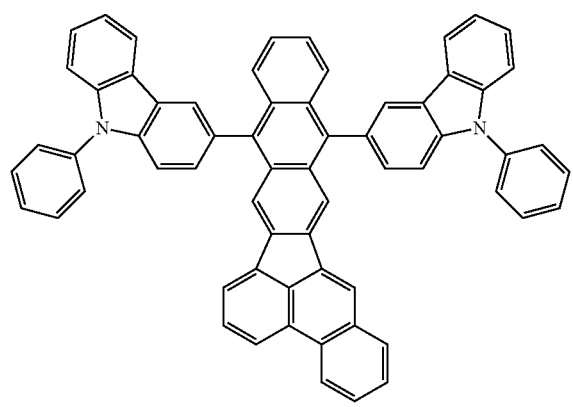
k-22
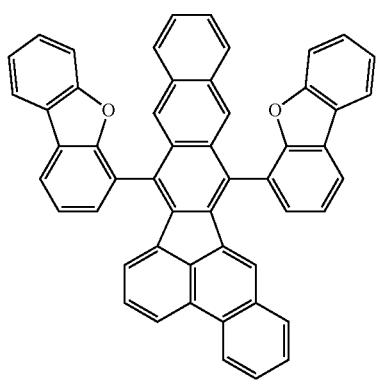
k-23
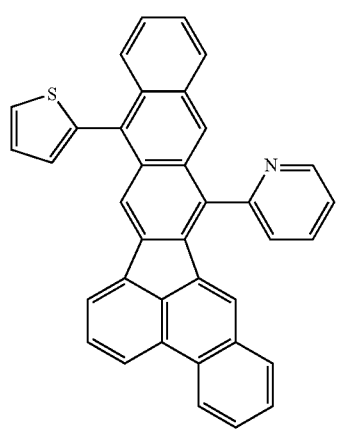
k-24
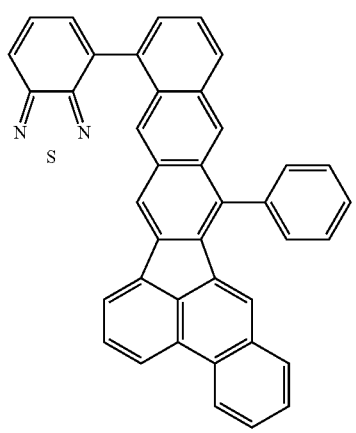

[Chem. 18]
k-25
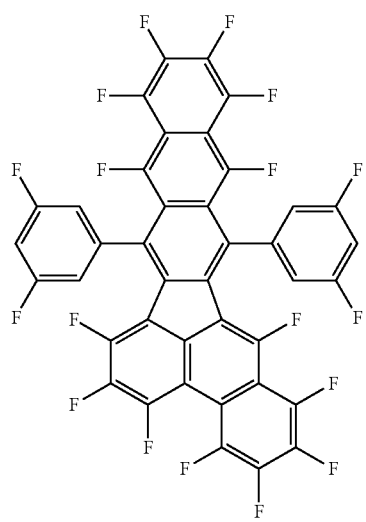
k-26
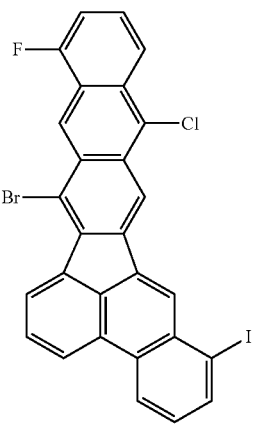
k-27
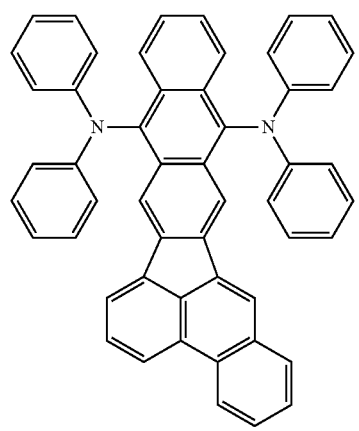
k-28
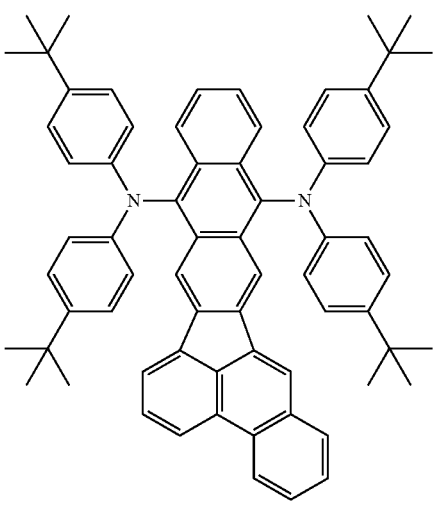
k-29
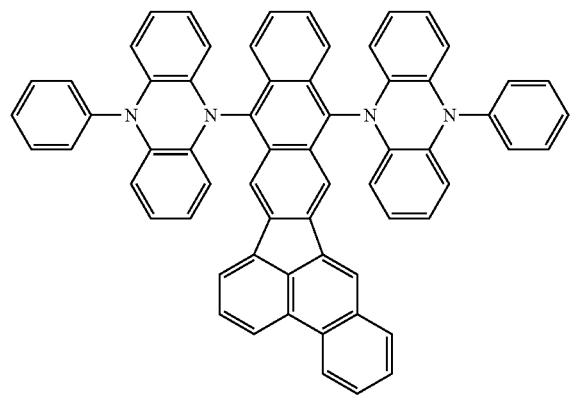
k-30
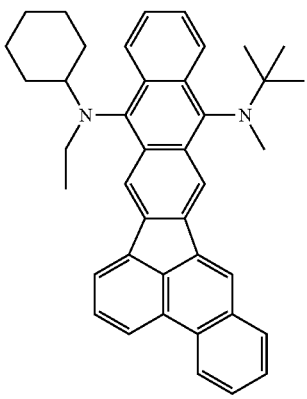

-continued
k-31
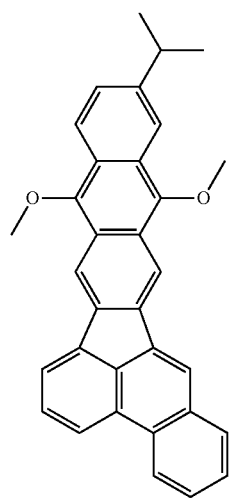
k-32
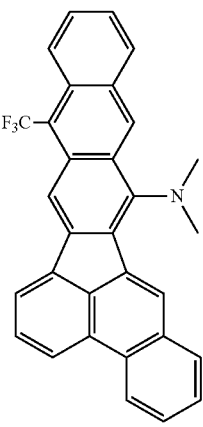
k-33
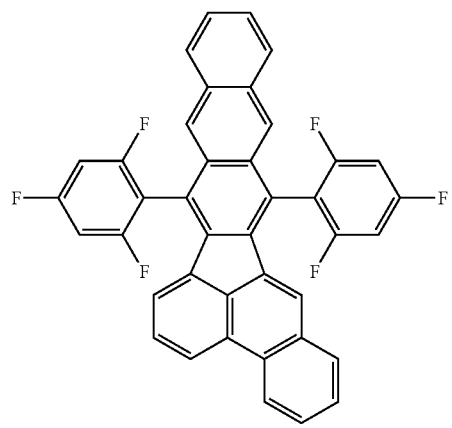
k-34
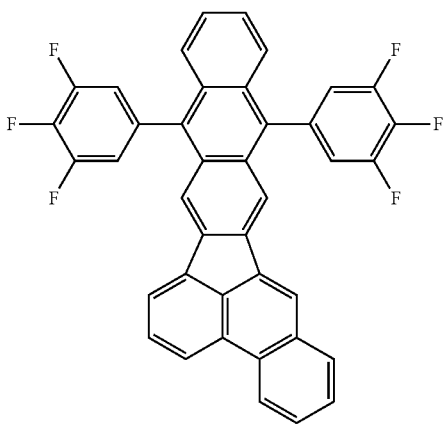
k-35
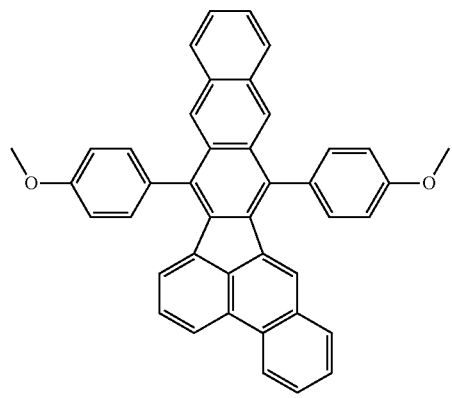
k-36
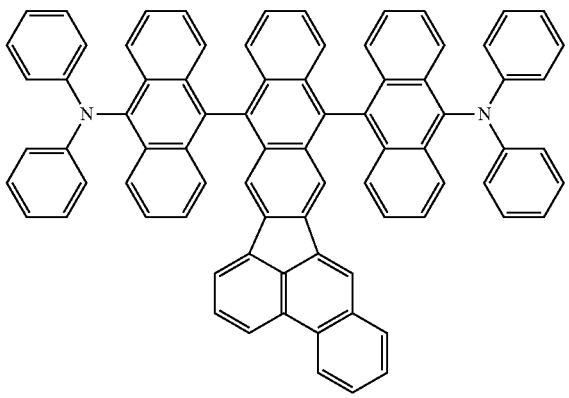

-continued

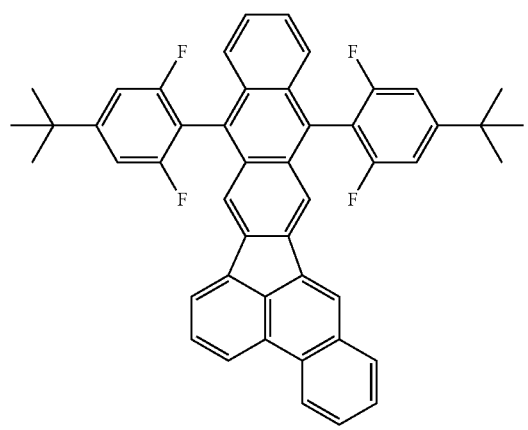
k-37

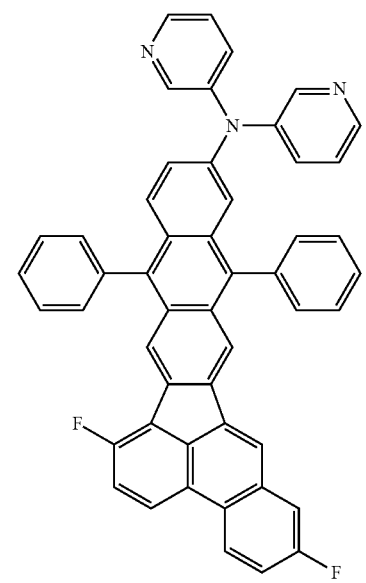
k-38

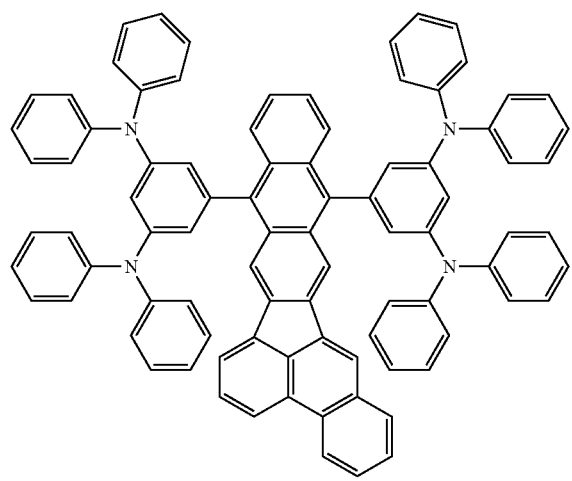
k-39

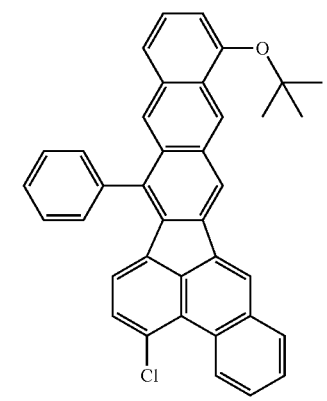
k-40

Next, an organic light-emitting element of the present invention will be described in detail.

An organic light-emitting element according to the present invention includes an anode, a cathode, and a layer composed of an organic compound and disposed between the anode and the cathode. At least one layer constituting the layer composed of an organic compound, i.e., the organic compound layer, contains a fused-ring aromatic compound of the present invention. The organic light-emitting element according to the present invention is preferably an organic light-emitting element that emits light when a voltage is applied between the anode and the cathode.

The organic compound layer may include a single layer or a plurality of layers. In the case where the organic compound layer includes a plurality of layers, the layers are composed of functional layers having individual functions. Specific examples of a layer structure of the organic light-emitting element will be described below.

A first specific example is a structure of an organic light-emitting element in which a substrate, an anode, a light-emitting layer, and a cathode are disposed in that order.

A second specific example is a structure of an organic light-emitting element in which a substrate, an anode, a hole-transporting layer, an electron-transporting layer, and a cathode are disposed in that order. In this case, a light-emitting layer includes the hole-transporting layer and the electron-transporting layer.

A third specific example is a structure of an organic light-emitting element in which a substrate, an anode, a hole-transporting layer, a light-emitting layer, an electron-transporting layer, and a cathode are disposed in that order.

A fourth specific example is a structure of an organic light-emitting element in which a substrate, an anode, a hole injection layer, a hole-transporting layer, a light-emitting layer, an electron-transporting layer, and a cathode are disposed in that order.

A fifth specific example is a structure of an organic light-emitting element in which a substrate, an anode, a hole-transporting layer, a light-emitting layer, a hole/exciton-blocking layer, an electron-transporting layer, and a cathode are disposed in that order.

A sixth specific example is a structure of an organic light-emitting element in which a substrate, an anode, a hole-transporting layer, a light-emitting layer, a hole/exciton-blocking layer, an electron-transporting layer, an electron injection layer, and a cathode are disposed in that order.

As described in these examples, the organic compound layer disposed between the anode and the cathode may be constituted by various functional layers. A compound according to the present invention may be contained in at least one of these functional layers, or a specific functional layer may contain a plurality of compounds according to the present invention.

The layer structure of an organic light-emitting element containing a fused polycyclic compound according to the present invention is not limited thereto. For example, an insulating layer, an adhesive layer, or an interference layer may be provided at an interface between an electrode and an organic layer. The hole-transporting layer may include two layers having different ionization potentials.

A fused polycyclic compound according to the present invention can be used in an organic light-emitting element having any one of the layer structures described in the above specific examples. In this case, the fused polycyclic compound of the present invention may be used alone or in combinations of two or more compounds.

A fused polycyclic compound according to the present invention can be preferably used as a material constituting any of the light-emitting layer, the hole-transporting layer, the electron-transporting layer, the hole injection layer, and the hole/exciton-blocking layer. In this case, the layer may be composed of a single fused polycyclic compound or a combination of two or more fused polycyclic compounds.

When a fused polycyclic compound according to the present invention is used as a host material of a light-emitting layer, a luminescent material used as a guest material is not particularly limited, but preferably a fluorescence-emitting material.

The emission wavelength of the guest material is preferably longer than the emission wavelength of the fused polycyclic compound according to the present invention. When light emitted from the fused polycyclic compound of the present invention is blue light, light emitted from the luminescent material used as the guest material is preferably green light to red light. More preferably, the guest material is a luminescent material that emits green light.

When the fused polycyclic compound according to the present invention is used as a host material of a light-emitting layer, the content of the fused polycyclic compound is preferably in the range of 50 to 99.9 percent by weight and more preferably in the range of 80 to 99.9 percent by weight of the total material constituting the light-emitting layer.

When the fused polycyclic compound according to the present invention is used as a guest material (luminescent material) of a light-emitting layer, the content of the fused polycyclic compound is preferably in the range of 0.1 to 50 percent by weight and more preferably in the range of 0.1 to 20 percent by weight of the total material constituting the light-emitting layer.

The compound represented by general formula [1] according to the present invention may be used as any layer in an organic light-emitting element. The compound represented by general formula [1] may be used in combination with a known hole transport material, a matrix material, a luminescent material, an electron transport material, or the like according to need. As anode materials used in an organic light-emitting element of the present invention, those having a work function as high as possible are preferable. Examples thereof include metal elements such as gold, platinum, nickel, palladium, cobalt, selenium, and vanadium; alloys thereof; and metal oxides such as tin oxide, zinc oxide, indium tin oxide (ITO), and indium zinc oxide. Alternatively, electrically conductive polymers such as polyaniline, polypyrrole, polythiophene, and polyphenylene sulfide can also be used. These electrode materials may be used alone or in combinations of two or more materials.

On the other hand, as cathode materials, those having a low work function are preferable. Examples of the cathode materials that can be used include metal elements such as lithium, sodium, potassium, cesium, calcium, magnesium, aluminum, indium, silver, lead, tin, and chromium; and alloys thereof. Metal oxides such as indium tin oxide (ITO) can also be used. The cathode may be composed of one layer or two or more layers.

The substrate used in the organic light-emitting element of the present invention is not particularly limited. Opaque substrates such as metal substrates and ceramic substrates, and transparent substrates such as glass, quartz, and plastic sheets can be used. The luminescent color can be controlled by providing a color filter film, a fluorescent color conversion filter film, a dielectric reflecting film, or the like on the substrate.

In addition, a protective layer or a sealing layer may be provided on the prepared organic light-emitting element for the purpose of preventing contact with oxygen, moisture, or the like. Examples of the protective layer include a diamond thin film; inorganic material films such as metal oxide films and metal nitride films; polymer films such as fluorocarbon resin films, a poly-para-xylylene film, a polyethylene film, silicone resin films, and a polystyrene resin film; and photocurable resin films. The element may be covered with, for example, glass, a gas-impermeable film, or a metal and packaged with a suitable sealing resin.

The organic compound layer containing a fused polycyclic compound of the present invention can be formed by a vacuum evaporation method, a cast method, an application method, a spin-coating method, an ink jet method, or the like.

The organic light-emitting element of the present invention can be applied to a product which needs energy saving and high luminance. Application examples of the organic light-emitting element of the present invention include display apparatuses, illuminating devices, light sources of a printer, and backlights of a liquid crystal display apparatus. As a display apparatus, a lightweight, flat-panel display that has a high visibility and that realizes energy saving can be realized. An organic light-emitting element according to the present invention is preferably used in a display unit of such a display apparatus. As a display apparatus, the organic light-emitting element of the present invention can also be used in an operation panel unit or a finder, i.e., a display unit, of an image pickup apparatus such as a digital video camera or a digital still camera.

As for a light source of a printer, a laser light source unit of laser beam printers that are currently widely used can be replaced with light-emitting elements of the present invention. Elements that can be independently addressed are arranged in the form of an array and a desired exposure is performed on a photosensitive drum, thereby forming an image. The use of the elements of the present invention can significantly decrease the volume of the apparatus. As for an illuminating device and a backlight, an effect of energy saving achieved by the present invention can be expected.

Organic light-emitting elements of the present invention can be used as passive matrix organic light-emitting elements. Alternatively, in the application to a display, a method in which the organic light-emitting elements are driven by a TFT driving circuit, which is used in an active matrix system, can also be employed. Either a source electrode or a drain electrode of each TFT is connected to either the anode or the cathode of the corresponding organic light-emitting element. The TFT controls the light-emission luminance of the organic light-emitting element.

EXAMPLES

The present invention will now be specifically described on the basis of Examples, but the present invention is not limited thereto.

Example 1

Synthesis of Exemplified Compound b-33

[Chem. 19]

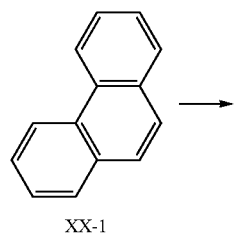

XX-1

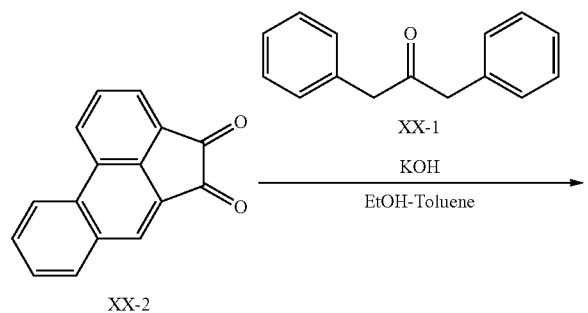

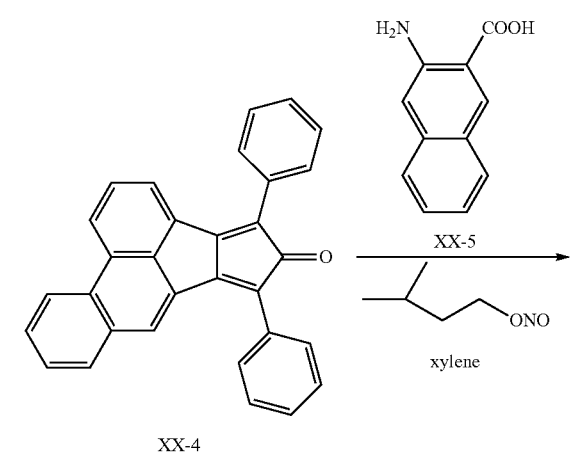

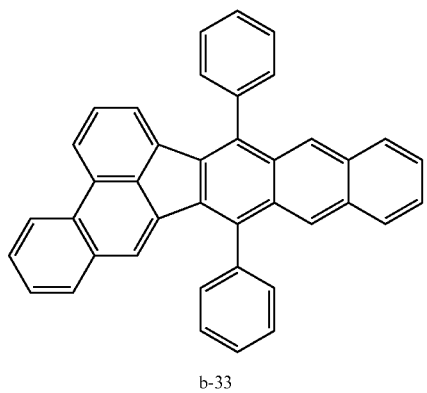

b-33

To a 20-mL reaction vessel, XX-2 (1.8 g, 7.7 mmol) synthesized in accordance with Journal of American Chemical Society, 91, 918 (1969), XX-3 (1.6 g, 7.7 mmol), and a mixed solvent (110 mL) of toluene and ethanol (toluene:ethanol=1:10 (w/w)) were added. A 0.5N-potassium hydroxide ethanol solution (20 mL) was gradually added dropwise to the resulting solution under stirring. The solution was heated to 75° C. and stirred for three hours at the same temperature. The solution was cooled to room temperature, and precipitated crystals were filtered. The crystals were washed with water and methanol to obtain XX-4 (1.8 g, yield: 58%).

Next, XX-4 (0.9 g, 2.2 mmol), xylene (60 mL), XX-5 (0.8 g, 4.4 mmol), and isoamyl nitrite (0.5 g, 4.4 mmol) were added to a 50-mL reaction vessel, and the resulting solution was stirred and refluxed for one hour.

The reaction solution was concentrated, and separated and purified by silica gel chromatography (mobile phase; chloroform:hexane=1:5). The purified product was recrystallized with toluene-ethanol to obtain Exemplified Compound b-33 in the form of a yellow powder (0.2 g, 0.38 mmol, yield: 18%)

The structure of the compound was confirmed by measuring a mass spectrum (MS) and a nuclear magnetic resonance (NMR) spectrum.

By measuring a matrix-assisted laser desorption/ionization mass spectrum (MALDI-MS), 504, which was an M+ of this compound, was confirmed.

$^1$H-NMR (CDCl$_3$, 500 MHz) σ (ppm): 8.57 (d, 1H), 8.37 (d, 1H), 8.19 (s, 1H), 8.16 (s, 1H), 7.85 (m, 4H), 7.81-7.64 (m, 10H), 7.60 (m, 2H), 7.51-7.45 (m, 2H), 7.40 (m, 2H), 6.82 (s, 1H), 6.69 (s, 1H).

Description of Emission Spectrum

FIG. 1 shows an emission spectrum of Exemplified Compound b-33. The maximum emission wavelength was 451 nm, which is a preferable emission wavelength as a blue-light-emitting material. As a result of a comparison of the emission quantum yield of Exemplified Compound b-33 with that of benzo[k]fluoranthene, which is known as a compound having a very high emission quantum yield, benzofluoranthene:Exemplified Compound b-33=1:1.03. Thus, Exemplified Compound b-33 had a very high emission quantum yield, which was equivalent to that of benzo[k]fluoranthene. According to this result, it was confirmed that the skeleton in the present invention had a very high emission quantum yield and was preferable as a material for an electroluminescence element.

Thermophysical properties were measured by differential scanning calorimetry (DSC). The DSC measurement was conducted with a Pyris DSC 1 calorimeter manufactured by PerkinElmer Co., Ltd.

As for the measurement of the glass transition temperature, a glass transition temperature determined when a glass state was formed and the temperature was then further increased at a temperature-increasing rate of 20 (° C./min) was defined as the glass transition temperature. In a step of decreasing the temperature from the melting point, the measurement was performed at a temperature-decreasing rate of 40 (° C./min).

The glass transition temperature of Exemplified Compound b-33 was 148° C. Even when an increase in the temperature was continued to a temperature (320° C.) over the glass transition temperature and the melting point of the compound, recrystallization was not observed.

This result suggests that Exemplified Compound b-33 according to the present invention has low crystallinity. This property suggests that a stable amorphous state that is not readily recrystallized can be formed. It is believed that this property is based on a low symmetry of the molecular skeleton of this compound.

Accordingly, the material of the present invention can also be preferably used as a host material or charge-transporting layer in which the stability of the quality of the resulting film is particularly required.

Example 2

An organic light-emitting element was produced. First, indium tin oxide (ITO) was deposited as an anode on a glass substrate (substrate) by a sputtering method so as to have a thickness of 120 nm. Next, the substrate was sequentially washed with acetone and isopropyl alcohol (IPA) using ultrasonic waves. Subsequently, the substrate was washed with IPA under boiling and then dried. Furthermore, the substrate was washed with UV/ozone. The substrate prepared as described above was used as a transparent electrically conductive support substrate.

Next, a chloroform solution of HTL-1 shown below was applied to the transparent electrically conductive support substrate by a spin-coating method to form a hole-transporting layer having a thickness of 11 nm.

Next, other organic layers and electrode layers were successively deposited in a vacuum chamber at a pressure of $10^{-5}$ Pa by a resistance-heating vacuum evaporation method to prepare an element.

Specifically, first, as a hole-transporting layer, HTL-2 which was a hole transport material shown below was deposited so as to have a thickness of 15 nm.

Next, as a light-emitting layer, HOST-1 which was a host material shown below and Exemplified Compound b-33 which was a guest material were codeposited so that the weight concentration ratio of HOST-1:Exemplified Compound b-33 was 98:2. In this step, the thickness of the light-emitting layer was controlled to be 30 nm. Next, as an electron-transporting layer, ETL-1 shown below was deposited so as to have a thickness of 30 nm. Next, as a first metal electrode layer, LiF was deposited so as to have a thickness of 0.5 nm. Lastly, as a second metal electrode layer, Al was deposited so as to have a thickness of 150 nm. The first metal electrode layer (LiF layer) and the second metal electrode layer (Al layer) function as a cathode. An organic light-emitting element was prepared as described above.

[Chem. 20]

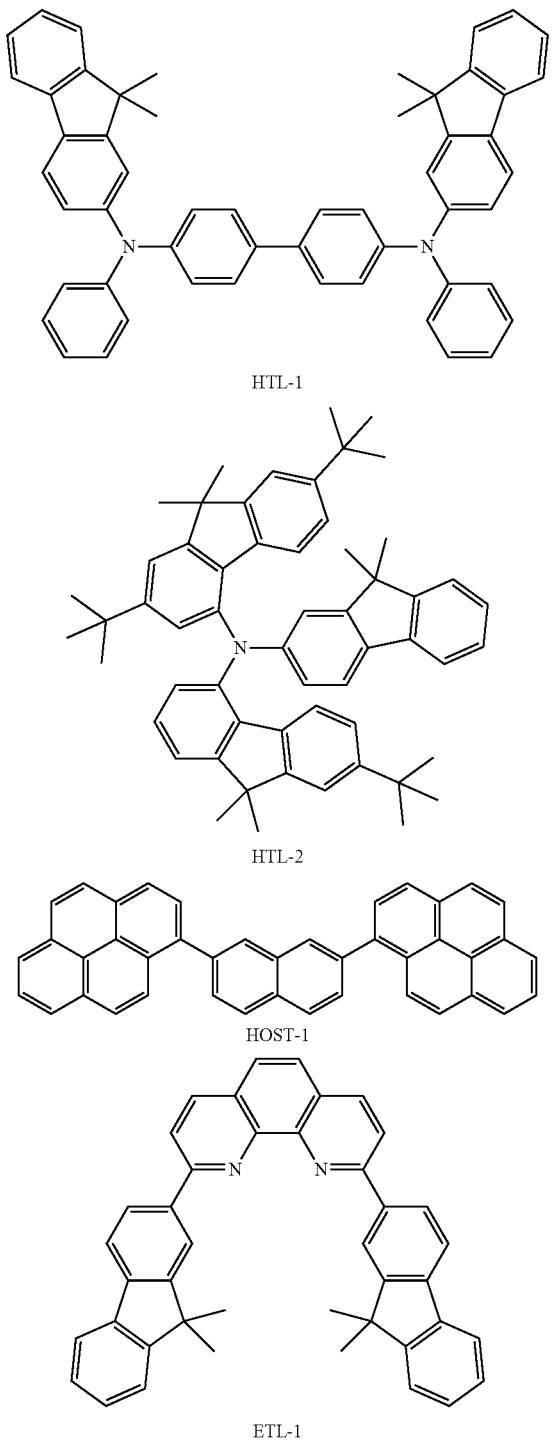

When a voltage of 4.0 V was applied to the element of this Example, blue-light emission was observed.

The element had an efficiency of 4.3 cd/A (500 cd/m$^2$). Furthermore, the element was continuously energized in a nitrogen atmosphere. As a result, stable light emission could be achieved even after continuous energization for 100 hours.

It was confirmed that an organic light-emitting element in which a material of the present invention was used as a luminescent material emitted light with high efficiency and stably emitted light for a long time.

Example 3

A thin-film transistor (TFT) was formed on a glass substrate used as a transparent substrate. A polyimide film was formed on the TFT. The polyimide film was then exposed, developed, and baked to form a planarizing film. A contact hole is formed in this stage so that an electrode formed in a subsequent step is connected to the TFT via the contact hole.

Next, an Al film having a thickness of 100 nm was deposited on the planarizing film. An insulating film composed of a polyimide resin for pixel separation was stacked on the Al film and patterned.

Furthermore, other organic layers and an electrode layer functioning as a cathode were successively deposited in a vacuum chamber at a pressure of $10^{-5}$ Pa by a resistance-heating vacuum evaporation method to prepare an organic light-emitting element.

Hole-transporting layer (110 nm): HTL-1
Light-emitting layer (20 nm): GUEST-1 (2 percent by weight) and Exemplified Compound b-33

[Chem. 21]

GUEST-1

Hole/exciton-blocking layer (10 nm): EBL-1

[Chem. 22]

EBL-1

Electron-transporting layer 1 (10 nm): ETL-2
Electron-transporting layer 2 (60 nm): $Cs_2CO_3$ (3 percent by weight) and ETL-2

As a cathode, an ITO film having a thickness of 50 nm was deposited thereon. The ITO film was deposited by a sputtering method.

When a voltage of 4.1 V was applied to the element of this Example, green-light emission with a light-emission luminance of 4,000 cd/m² was observed. When a voltage was applied to the element in a nitrogen atmosphere with a current density of 100 mA/cm², a high efficiency of 24,000 cd/m² was achieved. A CIE chromaticity of x=0.24 and y=0.69 was obtained. Thus, green-light emission with good color purity was observed. Furthermore, the element was continuously energized in a nitrogen atmosphere. As a result, stable light emission could be achieved even after continuous energization for 100 hours.

It was confirmed that an organic light-emitting element in which a material of the present invention was used as a host material of a green-light-emitting material emitted light with high efficiency and stably emitted light for a long time.

Example 4

Synthesis of Exemplified Compound b-1

[Chem. 23]

XX-6    XX-7    →AlCl₃

XX-8

(1) Synthesis of XX-8
The following reagents and solvent were charged in a reaction vessel.
XX-6: 40 g (170 mmol)
XX-7: 6.2 g (42 mmol)
$AlCl_3$: 10 g Next, argon was introduced into the reaction vessel to replace the atmosphere of the reaction system with argon. Next, the reaction solution was heated to 80° C. and stirred at this temperature for two hours. Subsequently, the reaction solution was cooled, and a 1.0 M aqueous solution of HCl was added thereto. The resulting reaction solution was separated with chloroform, and an organic layer was recovered. Next, the organic layer was dried under sodium sulfate, and the solvent was then distilled off under a reduced pressure. Thus, a crude product was obtained. Next, the crude product was recrystallized with toluene, thereby obtaining 9.2 g of XX-8 (yield: 56%).

[Chem. 24]

XX-8  →$H_2SO_4$

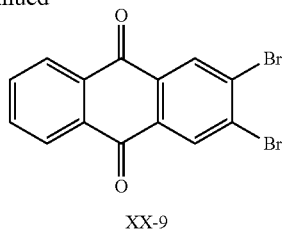

XX-9

(2) Synthesis of XX-9
The following reagent and solvent were charged in a reaction vessel.
XX-8: 6 g (15.6 mmol)
Concentrated sulfuric acid: 30 mL Next, argon was introduced into the reaction vessel to replace the atmosphere of the reaction system with argon. Next, the reaction solution was heated to 130° C. and stirred at this temperature for two hours. Subsequently, the reaction solution was cooled to room temperature, and precipitated crystals were filtered. Next, the crystals were sequentially washed with water and methanol, thereby obtaining 3.6 g of XX-9 (yield: 63%).

[Chem. 25]

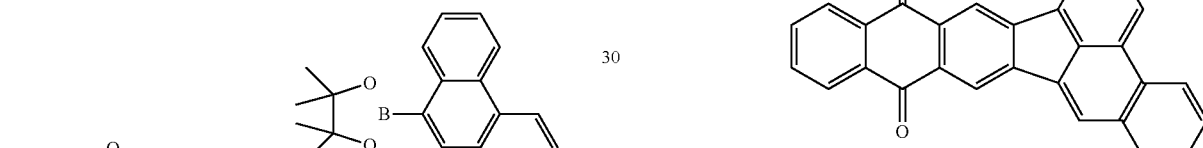

XX-9

XX-11

(3) Synthesis of XX-11
The following reagents and solvents were charged in a reaction vessel.
XX-9: 3 g (8.2 mmol)
XX-10: 2.5 g (8.2 mmol)
Toluene: 40 mL
Ethanol: 10 mL
2 M aqueous solution of sodium carbonate: 10 mL Next, argon was introduced into the reaction vessel to replace the atmosphere of the reaction system with argon. Furthermore, 150 mg of tetrakis(triphenylphosphine)palladium was added to the reaction solution. Next, the reaction solution was heated to 75° C. and stirred at this temperature for 12 hours. Subsequently, the reaction solution was cooled, and precipitated crystals were filtered. Next, the crystals were sequentially washed with water and methanol, thereby obtaining 2.4 g of XX-11 (yield: 64%).

[Chem. 26]

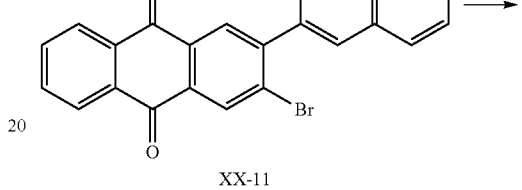

XX-11

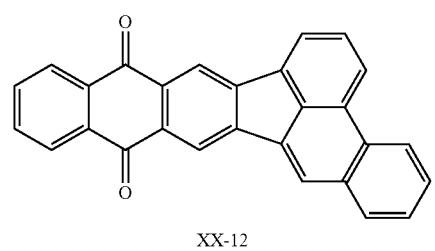

XX-12

(4) Synthesis of XX-12
The following reagents and solvent were charged in a reaction vessel.
XX-11: 2 g (4.4 mmol)
Diazabicycloundecene: 2 g
Dimethylformamide: 100 mL Next, argon was introduced into the reaction vessel to replace the atmosphere of the reaction system with argon. Furthermore, 150 mg of bis(triphenylphosphine)palladium dichloride was added to the reaction solution. Next, the reaction solution was heated to 120° C. and stirred at this temperature for two hours. Subsequently, the reaction solution was cooled, and precipitated crystals were filtered. Next, the crystals were sequentially washed with water and methanol, thereby obtaining 1 g of XX-12 (yield: 60%).

[Chem. 27]

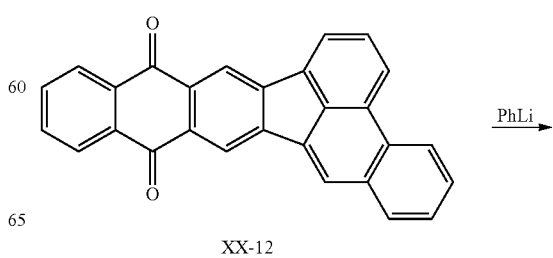

XX-12

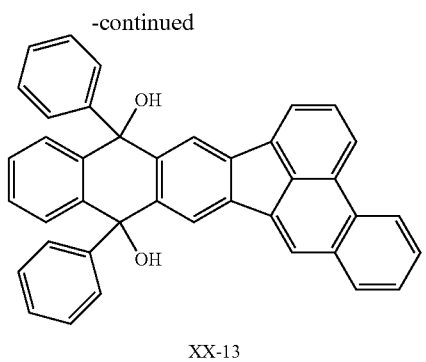

XX-13

(5) Synthesis of XX-13

The following reagent and solvent were charged in a reaction vessel.

XX-12: 1 g (2.6 mmol)
THF: 50 mL

Next, argon was introduced into the reaction vessel to replace the atmosphere of the reaction system with argon. The reaction solution was then cooled to −78° C. in a dry ice bath. Next, 4 mL of a 1.9 M phenyllithium solution was added dropwise thereto, and the reaction solution was stirred at room temperature for two hours. After the completion of the reaction, the reaction solution was poured into ice water. Ethyl acetate was added thereto to separate the resulting solution, and an organic layer was recovered. Next, this organic layer was dried over sodium sulfate, and the solvent was then distilled off under a reduced pressure. Thus, a crude product was obtained. This crude product was separated and purified by silica gel chromatography (developing solvent: heptane/ethyl acetate=3/1). Next, the purified product was recrystallized from toluene-ethanol, thereby 630 mg of XX-13 (yield: 45%).

[Chem. 28]

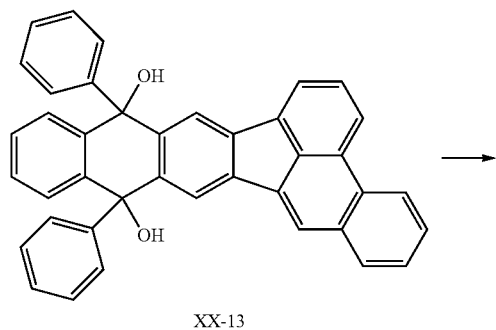

XX-13

→

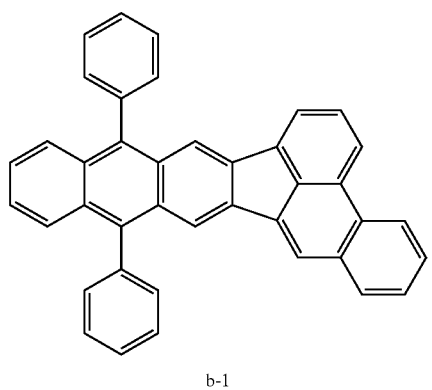

b-1

(6) Synthesis of Exemplified Compound b-1

The following reagents and solvent were charged in a 50-mL reaction vessel.

XX-13: 0.5 g (0.9 mmol)
NaH$_2$PO$_2$·H$_2$O: 1.6 g (19 mmol)
Potassium iodide: 1.2 g (7.5 mmol)
Acetic acid: 50 mL Next, argon was introduced into the reaction vessel to replace the atmosphere of the reaction system with argon. Next, the reaction solution was heated to 80° C. and stirred at this temperature for 12 hours. After the completion of the reaction, the reaction solution was poured into ice water, and precipitated crystals were filtered. Thus, a crude product was obtained. This crude product was separated and purified by silica gel chromatography (developing solvent: heptane/toluene=6/1). Next, the purified product was recrystallized from toluene-ethanol, thereby obtaining 61 mg of Exemplified Compound b-1 as a yellow powder (yield: 14%).

The structure of the compound was confirmed by measuring a mass spectrum (MS) and a nuclear magnetic resonance (NMR) spectrum. Specifically, by measuring a matrix-assisted laser desorption/ionization mass spectrum (MALDI-MS), 504, which was an M+ of this compound, was confirmed. The measurement result of the NMR is shown below.

$^1$H-NMR (CDCl$_3$, 400 MHz) σ (ppm): 8.64 (d, 1H), 8.45 (d, 1H), 8.28 (s, 1H), 8.16 (s, 1H), 8.11 (s, 1H) 7.95 (m, 2H), 7.75-7.55 (m, 14H), 7.36-7.33 (m, 3H).

Figure 2:
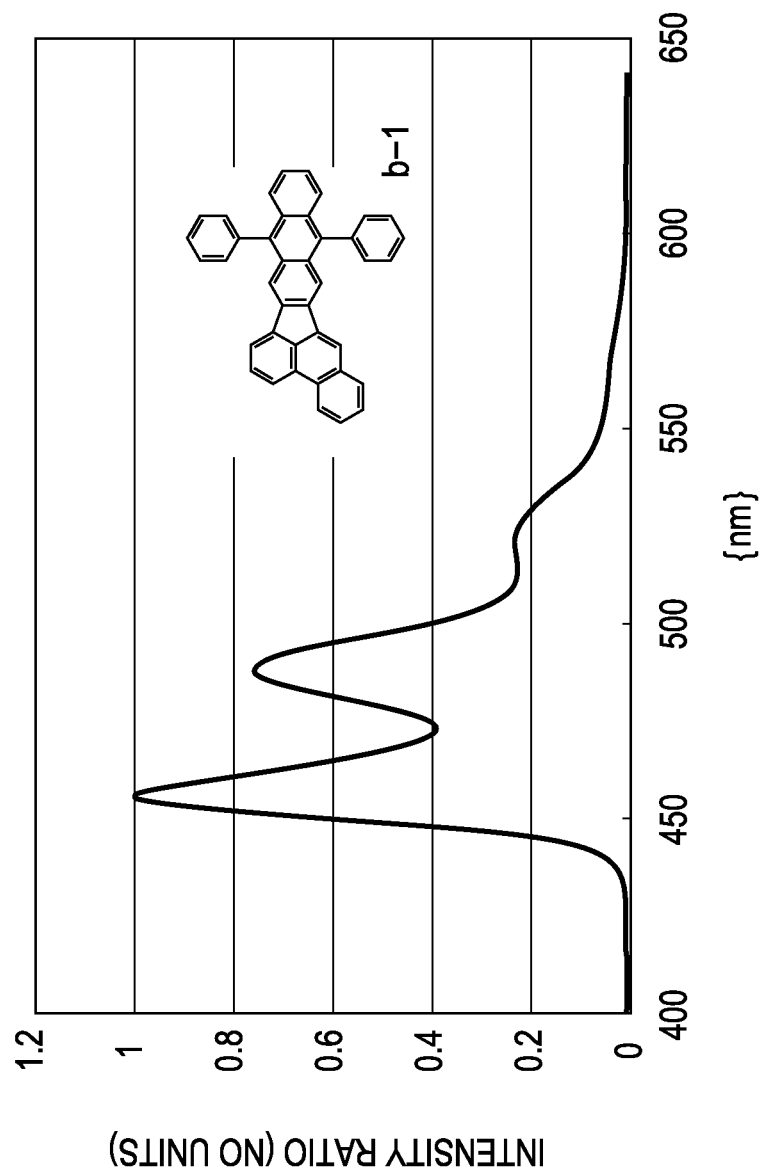
FIG. 2 shows an emission spectrum of Exemplified Compound b-1.

FIG. 2 shows an emission spectrum of Exemplified Compound b-1. The maximum emission wavelength was 456 nm, which is a preferable emission wavelength as a blue-light-emitting material. As a result of a comparison of the emission quantum yield of Exemplified Compound b-1 with that of benzo[k]fluoranthene, which is known as a compound having a very high emission quantum yield, benzofluoranthene:Exemplified Compound b-1=1:0.93. Thus, Exemplified Compound b-1 had a very high emission quantum yield, which was equivalent to that of benzo[k]fluoranthene. According to this result, it was confirmed that the skeleton in the present invention had a very high emission quantum yield and was preferable as a material for an electroluminescence element.

Furthermore, thermophysical properties were measured by DSC by the same method as that used in Example 1. The glass transition temperature of Exemplified Compound b-1 was 159° C. Even when an increase in the temperature was continued to a temperature (220° C.) over the glass transition temperature and the melting point of the compound, recrystallization was not observed. This result suggests that Exemplified Compound b-1 according to the present invention has low crystallinity. This property suggests that a stable amorphous state that is not readily recrystallized can be formed. It is believed that this property is based on a low symmetry of the molecular skeleton of this compound.

Accordingly, the material of the present invention can also be preferably used as a host material or charge-transporting layer in which the stability of the quality of the resulting film is particularly required.

Example 5

An element was produced by the same method as that used in Example 2 except that the Exemplified Compound b-1 was used as the guest material of the light-emitting layer in Example 2 instead of Exemplified Compound b-33.

When a voltage of 4.5 V was applied to the organic light-emitting element of this Example, blue-light emission was observed.

The element had an efficiency of 3.3 cd/A (500 cd/m$^2$).

Furthermore, the element was continuously energized in a nitrogen atmosphere. As a result, stable light emission could be achieved even after continuous energization for 100 hours.

It was confirmed that an organic light-emitting element in which a material of the present invention was used as a luminescent material emitted light with high efficiency and stably emitted light for a long time.

Example 6

An element was produced by the same method as that used in Example 2 except that GUEST-2 was used as the guest material of the light-emitting layer in Example 2 instead of Exemplified Compound b-33, and Exemplified Compound b-1 was used as the host material instead of HOST-1.

When a voltage of 5.4 V was applied to the organic light-emitting element of this Example, yellow-green-light emission was observed.

The element had an efficiency of 16.1 cd/A (1,000 cd/m$^2$). Furthermore, the element was continuously energized in a nitrogen atmosphere. As a result, stable light emission could be achieved even after continuous energization for 100 hours.

It was confirmed that an organic light-emitting element in which a material of the present invention was used as a host material emitted light with high efficiency and stably emitted light for a long time.

[Chem. 29]

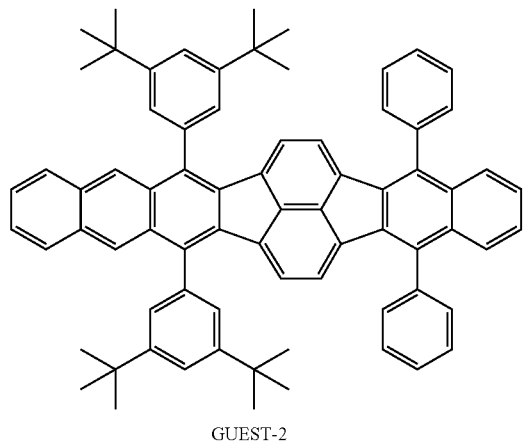

GUEST-2

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-304601, filed Nov. 28, 2008 and Japanese Patent Application No. 2009-245813, filed Oct. 26, 2009, which are hereby incorporated by reference herein in their entirety.

The invention claimed is:

1. An organic light-emitting element comprising:
   an anode;
   a cathode; and
   an organic compound layer disposed between the anode and cathode,
   wherein the organic compound layer contains the fused polycyclic compound represented by general formula [1];

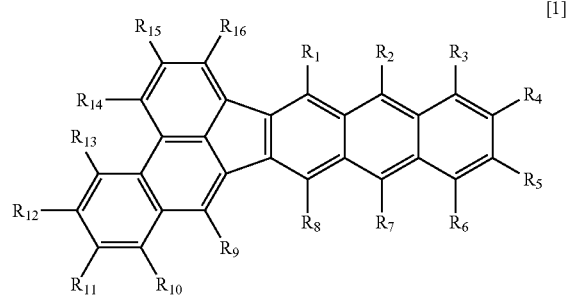

wherein $R_1$ to $R_{16}$ are each independently selected from a hydrogen atom, a halogen atom, an alkyl group having 1 to 20 carbon atoms, a substituted amino group, an aryl group which may have a substituent, and a heterocyclic group which may have a substituent, however, at least one of $R_1$ to $R_{16}$ is selected from a halogen atom, an alkyl group having 1 to 20 carbon atoms, a substituted amino group, an aryl group which may have a substituent, and a heterocyclic group which may have a substituent.

2. The organic light-emitting element according to claim 1, wherein the organic compound layer is a light-emitting layer.

3. The organic light-emitting element according to claim 2, wherein the light-emitting layer is composed of a host material and a guest material.

4. The organic light-emitting element according to claim 3, wherein the guest material is the fused polycyclic compound.

5. The organic light-emitting element according to claim 3, wherein the host material is the fused polycyclic compound.

6. An organic light-emitting element according to claim 5, wherein the organic light-emitting element emits a light which contains green light.

7. The organic light-emitting element according to claim 1, wherein the organic light-emitting element is an organic light-emitting element that emits light when a voltage is applied between the anode and cathode.

8. A display apparatus comprising:
   a display unit including the organic light-emitting element according to claim 7.

9. An image pickup apparatus comprising:
   the display apparatus according to claim 8.

10. The display apparatus according to claim 8, further comprising a TFT connected to the light-emitting element.

11. The display apparatus according to claim 10, wherein the organic light-emitting element is driven by an active matrix method.

12. The display apparatus according to claim 8, wherein the organic light-emitting element is disposed on a transparent substrate.

13. The display apparatus according to claim 8, wherein the organic light-emitting element is disposed on an opaque substrate.

14. The display apparatus according to claim 8, further comprising a color filter film.

15. The display apparatus according to claim 8, further comprising a fluorescent color conversion filter film.

16. The display apparatus according to claim 8, further comprising a dielectric reflecting film.

17. The display apparatus according to claim 8, wherein the display apparatus is a finder.

18. The organic light-emitting element according to claim 1, wherein at least one of $R_1$, $R_8$, $R_2$, and $R_7$ is selected from a halogen atom, an alkyl group having 1 to 20 carbon atoms, a substituted amino group, an aryl group which may have a substituent, and a heterocyclic group which may have a substituent.

19. The organic light-emitting element according to claim 1, wherein each of $R_1$ and $R_8$ is an aryl group.

20. The organic light-emitting element according to claim 1, wherein each of $R_2$ and $R_7$ is an aryl group.

21. An illuminating device comprising the organic light-emitting element according to claim 1.

22. An image forming apparatus comprising: a photosensitive drum, and a light source by which the photosensitive drum is exposed to light, wherein the light source has the organic light-emitting element according to claim 1.

* * * * *